US012753155B2

(12) United States Patent
Cooks et al.

(10) Patent No.: US 12,753,155 B2
(45) **Date of Patent: *Oct. 6, 2026**

(54) METHODS OF COUPLING A CARBON CONTAINING MOIETY TO AN AMINE CONTAINING MOIETY

(71) Applicant: Purdue Research Foundation, West Lafayette, IN (US)

(72) Inventors: Robert Graham Cooks, West Lafayette, IN (US); Pallab Basuri, Chennai (IN); Nicolás M. Morato, West Lafayette, IN (US); Thalappil Pradeep, Madras (IN)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/367,032

(22) Filed: Sep. 12, 2023

(65) Prior Publication Data

US 2024/0025861 A1 Jan. 25, 2024

Related U.S. Application Data

(63) Continuation of application No. 17/323,290, filed on May 18, 2021, now Pat. No. 11,787,770.

(60) Provisional application No. 63/026,852, filed on May 19, 2020.

(51) Int. Cl.

| | |
|---|---|
| ***C07D 235/08*** | (2006.01) |
| ***C07D 235/02*** | (2006.01) |
| ***C07D 235/06*** | (2006.01) |
| ***C07D 235/10*** | (2006.01) |

(52) U.S. Cl.

CPC ......... *C07D 235/08* (2013.01); *C07D 235/02* (2013.01); *C07D 235/06* (2013.01); *C07D 235/10* (2013.01)

(58) Field of Classification Search

CPC .. C07D 235/08; C07D 235/02; C07D 235/06; C07D 235/10

See application file for complete search history.

(56) References Cited

U.S. PATENT DOCUMENTS

| | | | |
|---|---|---|---|
| 7,361,311 | B2 | 4/2008 | Cooks et al. |
| 9,184,036 | B2 | 11/2015 | Cooks et al. |
| 9,500,623 | B2 | 11/2016 | Cooks et al. |
| 2014/0051180 | A1 | 2/2014 | Cooks et al. |

FOREIGN PATENT DOCUMENTS

| | | | |
|---|---|---|---|
| WO | 2009/102766 | A1 | 8/2009 |

OTHER PUBLICATIONS

Badu-Tawiah AK, Campbell DI, Cooks RG. Accelerated C—N bond formation in dropcast thin films on ambient surfaces. J. Am. Soc. Mass Spectrom. Sep. 2012;23(9):1461-8. (Year: 2012).*

Badu-Tawiah, 2012, Accelerated C—N bond formation in dropcast thin films on ambient surfaces, J Am Soc Mass Spectrom 23:1461-1468.

Badu-Tawiah, 2012, Peptide Cross-linking at Ambient Surfaces by Reactions of Nanosprayed Molecular Cations, Angewandte Chemie International Edition, 124:9551-9555.

Bain, 2016, Accelerated hydrazone formation in charged microdroplets, Rapid Communications in Mass Spectrometry, 30:1875-7878.

Banerjee, 2015, Syntheses of Isoquinoline and Substituted Quinolines in Charged Microdroplets, Angew. Chem. Int. Ed., vol. 54: pp. 14795-14799.

Carroll, 1975, Atmospheric Pressure Ionization Mass Spectrometry: Corona Discharge Ion Source for Use in Liquid Chromatograph-Mass Spectrometer-Computer Analytical System, Anal. Chem. 47:2369-2373.

Cody, 2005, Versatile New Ion Source for the Analysis of Materials in Open Air under AMbient Conditions, Anal Chem, 77:2297-2302.

Fenn, 1989, Electrospray ionization for mass spectrometry of large biomolecules, Science, 246:64-71.

Fico, 2007, Miniaturization and Geometry Optimization of a Polymer-Based Rectilinear Ion Trap, Anal. Chem., 79:8076-8082.

Gao, 2006, Handheld Rectilinear Ion Trap Mass Spectrometer, Anal, 78:5994-6002.

Gao, 2008, Design and Characterization of a Multisource Hand-Held Tandem Mass Spectrometer, Anal Chem, 80:7198-7205.

Girod, 2011, Accelerated bimolecular reactions in microdroplets studied by desportion electrospray ionization mass spectrometry, Chem. Sci., vol. 2: pp. 501-510.

Hou, 2011, Sampling Wand for an Ion Trap Mass Spectrometer, Anal. Chem., 83:1857-1861.

Karas, 2000, Nano-electrospray ionization mass spectrometry: addressing analytical problems beyond routine, Fresenius J. Anal. Chem., 366:669-676.

Kogelschatz, 2003, Dielectric-Barrier Discharges: Their History, Discharge Physics, and Industrial Applications, Plasma Chemistry and Plasma Processing, 23:1-46.

Laiko, 2000, Atmospheric Pressure Matrix-Assisted Laser Desoprtion/Ionization Mass Spectrometry, Analytical Chemistry, 72:652-657.

Mulligan, 2006, Desorption electrospray ionization with a portable mass spectrometer: in situ analysis of ambient surfaces, Chem Comm, et al., Chemical Communications, 1709-1711.

Ouyang, 2009, Handheld Miniature Ion Trap Mass Spectrometers, Anal Chem., 81(7):2421-2425.

Ouyang, 2009, Miniature Mass Spectrometers, Ann Rev Anal Chem, 2:187-214.

Pan, 2004, Nanoelectrospray Ionization of Protein Mixtures: Solution pH and Protein p/, Anal. Chem., 76:1165-1174.

Saidykhan, 2017, Accelerated generation of (protonated) imines and quinoxalines by formation of C=N bonds in the microdroplets of a nebuliser, European Journal of Mass Spectrometry, 24:3-11.

Sanders, 2009, Hand-held mass spectrometer for environmentally relevant analytes using a variety of sampling and ionization methods, Euro J Mass Spectrom, 16:11-20.

(Continued)

*Primary Examiner* — James H Alstrum-Acevedo
*Assistant Examiner* — Pierre Paul Eleniste
(74) *Attorney, Agent, or Firm* — Brown Rudnick LLP; Adam M. Schoen

(57) ABSTRACT

The invention generally relates to methods of coupling a carbon containing moiety to an amine containing moiety.

18 Claims, 28 Drawing Sheets

(56) References Cited

OTHER PUBLICATIONS

Shiea, 2005, Electrospray-assisted laser desorption/ionization mass spectrometry for direct ambient analysis of solids, J. Rapid Communications in Mass Spectrometry, 19:3701-3704.
Sokol, 2011, Miniature mass spectrometer equipped with electrospray and desorption electrospray ionization for direct analysis of organics from solids and solutions, Int J Mass Spectrom, 306(2-3):187-195.
Takats, 2004, Electronsonic Spray Ionization. A Gentle Technique for Generating Folded Proteins and Protein Complexes in the Gas Phase and for Studying Ion-Molecule Reactions at Atmospheric Pressure, Anal. Chem., 76(14):4050-4058.
Tanaka, 1988, Protein and polymer analyses up to m/z 1000000 by laser ionization time-of-flight mass spectrometry, Rapid Commun. Mass Spectrom., 2:151-153.
Wei, 2017, Reaction Acceleration in Thin Films with Continuous Product Deposition for Organic Synthesis, Angewandte Chemie International Edition, 56(32):9386-9390.
Wei, 2018, High yield accelerated reactions in nonvolatile microthin films: chemical derivatization for analysis of single-cell intracellular fluid, Chemical Science, 7779-7786.
Xu, 2010, Miniaturization of Mass Spectrometry Analysis Systems, JALA, 15:433-439.
Yamashita, 1984, Electrospray ion source. Another variation on the free-jet theme, J. Phys. Chem., 88:4451-4459.
Yan, 2013, Chemical Reactivity Assessment Using reactive Paper Spray Ionization Mass Spectrometry: The Katritzky Reaction, ChemPlusChem, 78:1142-1148.

* cited by examiner

METHODS OF COUPLING A CARBON CONTAINING MOIETY TO AN AMINE CONTAINING MOIETY

RELATED APPLICATION

The present application is a continuation of U.S. nonprovisional application Ser. No. 17/323,290, filed May 18, 2021, which claims the benefit of and priority to U.S. provisional patent application Ser. No. 63/026,852, filed May 19, 2020, the content of each of which is incorporated by reference herein in its entirety.

GOVERNMENT SUPPORT

This invention was made with government support under grant number CHE1905087 awarded by the National Science Foundation. The government has certain rights in the invention.

FIELD OF THE INVENTION

The invention generally relates to methods of coupling a carbon containing moiety to an amine containing moiety.

BACKGROUND

Carbon-nitrogen (C—N) coupling chemistry is of comparable or even greater importance than carbon-carbon coupling in the context of pharmaceutically active small molecules. These reactions involve in situ conversion of precatalysts (often ligated Pd) to the active catalyst and activation of the amine by base, increasingly an organic base, so permitting reaction in a homogeneous liquid phase. An enormous number of catalysts have been explored and C—N bond formation is currently possible under relatively mild conditions using Pd, Cu and other organometallic catalysts. Conceptually, an alternative to nucleophilic substitution at an aryl or alkyl (pseudo) halide is acid catalyzed nucleophilic substitution at a carbonyl carbon, effectively amine addition to an acylium ion.

SUMMARY

The invention provides methods of coupling a carbon containing moiety to an amine containing moiety using microdroplets to create unique environments that facilitate and accelerate reactions as compared to bulk reactions. Particularly exemplified is a metal-free novel route for the accelerated synthesis of benzimidazole and its derivatives in the ambient atmosphere. The synthetic procedure involves 1,2-aromatic diamines and alkyl or aryl carboxylic acids reacting in electrostatically charged microdroplets generated using a nano-electrospray (nESI) ion source. The reactions are accelerated by orders of magnitude in comparison to the bulk. No other acid, base or catalyst is used. Online analysis of the microdroplet accelerated reaction products was performed by mass spectrometry. We provide evidence for an acid catalyzed reaction mechanism based on the identification of the intermediate arylamides. Their dehydration to give benimidazole products occurs in the rate determining thermally enhanced step. It is suggested that the extraordinary acidity at the droplet surface allows the carboxylic acid to function as a C-centered nucleophile. Comparisons of this methodology with data from thin film and bulk synthesis increases understanding of the microdroplet chemistry. Ten examples are shown as evidence of the scope of this chemistry. The accelerated synthesis has been scaled-up to establish the substituent-dependence and isolate products for NMR characterization.

In certain aspects, the invention provides methods of coupling a carbon containing moiety to an amine containing moiety that involve generating a microdroplet comprising a carbon containing moiety and an amine containing moiety, wherein the microdroplet comprises an acidic surface that facilitates a reaction between the carbon containing moiety and the amine containing moiety and generates a reaction product comprising a carbon-nitrogen bond via the amine of the amine containing moiety. Generating the microdroplets may be by use of an electrospray probe or nano-electrospray probe. The microdroplet may generate an environment that accelerates a rate of the reaction as compared to the same reaction occurring outside of a microdroplet environment.

In certain embodiments, the method further comprises analyzing the reaction product in a mass spectrometer by directing the microdroplets into the mass spectrometer. In certain embodiments, the method further comprises collecting the reaction product by directing the microdroplets onto a surface. In certain embodiments, the method is conducted without use of a metal or metal catalyst. In certain and or additional embodiments, the method is conducted without use of a base, that is the method is conducted without using a metal and/or a base.

In certain embodiments, the carbon containing moiety comprises a carboxylic acid, the amine containing moiety comprises an aromatic-1,2-diamine, and the reaction product is a benzimidazole.

Other aspects of the invention provide methods of producing a benzimidazole that involve generating a microdroplet comprising a carboxylic acid and an aromatic-1,2-diamine, wherein the microdroplet comprises an acidic surface that facilitates a reaction between the carboxylic acid and the aromatic-1,2-diamine and generates a benzimidazole. Generating the microdroplets may be by use of an electrospray probe or nano-electrospray probe. The microdroplet may generate an environment that accelerates a rate of the reaction as compared to the same reaction occurring outside of a microdroplet environment.

In certain embodiments, the method further comprises analyzing the benzimidazole in a mass spectrometer by directing the microdroplets into the mass spectrometer. In certain embodiments, the method further comprises collecting the benzimidazole by directing the microdroplets onto a surface. In certain embodiments, the method is conducted without use of a metal or metal catalyst. In certain and or additional embodiments, the method is conducted without use of a base, that is the method is conducted without using a metal and/or a base.

In certain embodiments, there is a 1:1 molar ratio of the aromatic-1,2-diamine and the carboxylic acid. In certain embodiments, a solvent in the microdroplet is methanol. In certain embodiments, the aromatic-1,2-diamine is at least one selected from the group consisting of: 1,2-phenyldiamine (PDA), 4-methyl-1,2-phenyldiamine, 4,5-dimethyl-1,2-phenyldiamine, 4-nitro-1,2-phenyldiamine, 4-chloro-1,2-phenyldiamine, 4-methoxy-1,2-phenyldiamine, 1,2-diaminonapthalene); and the carboxylic acid is at least one selected from the group consisting of: (formic acid (FA), acetic acid (AA), trifluoroacetic acid (TFAA), propanoic acid (PA) and benzoic acid (BA)).

DETAILED DESCRIPTION

Figure 1:
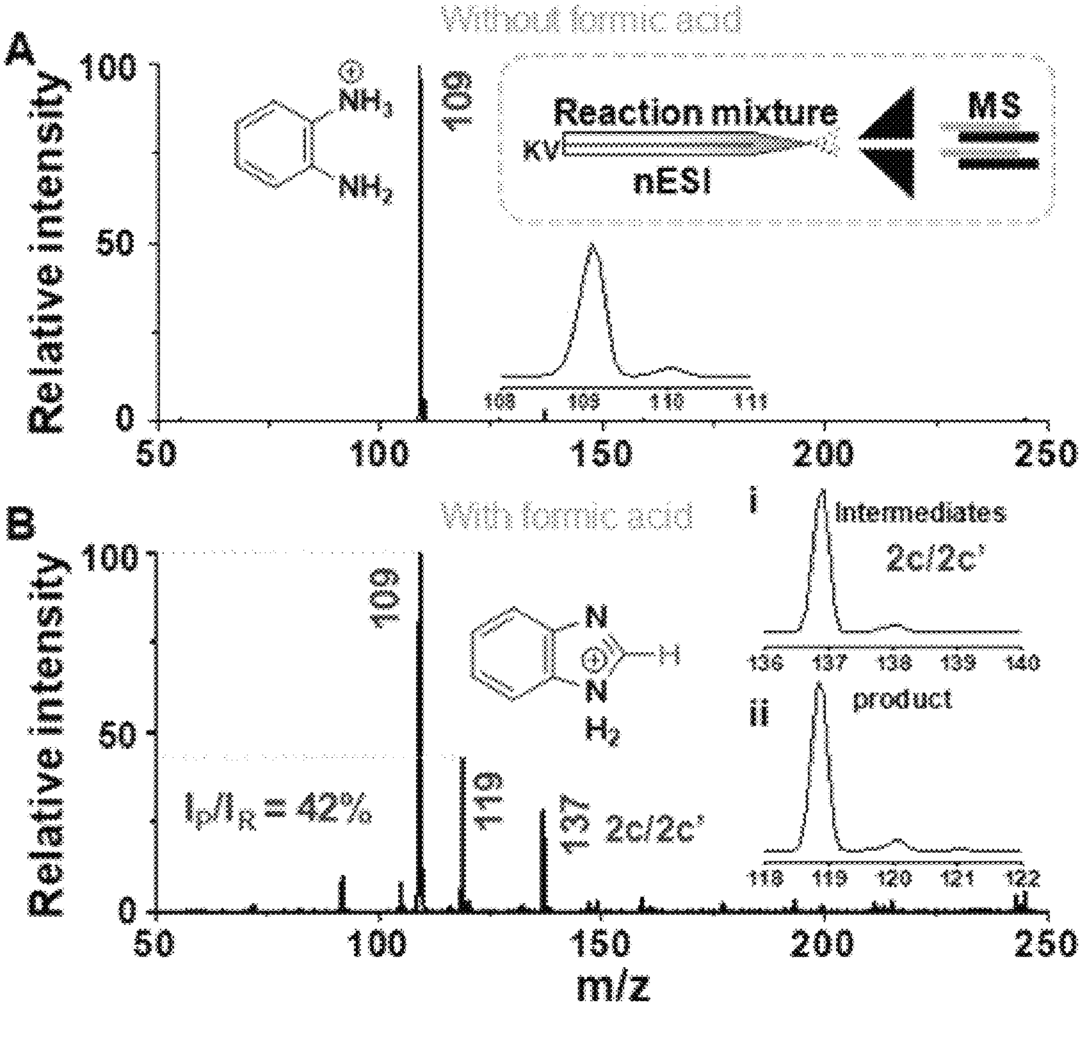
FIG. 1 panels A-B show microdroplets synthesis of benzimidazole. Panel A. Mass spectrum of PDA in methanol without addition of formic acid. Inset of the figure shows the isotopic distribution of the peak at m/z 109 and schematic illustration of the setup. Panel B. Mass spectrum of PDA with FA at 1:1 molar ratio in methanol. Inset shows the Intensity ratio between the product and the reactant ion. Insets show the isotopic distributions of the peaks at (i) m/z 137 and (ii) m/z 119. IP and IR refer to the intensity of signals for product and reactant, respectively.

The invention recognizes that the extraordinarily high acidity at the surface of aqueous droplets may drive these rapid reactions, even in cases like that in this study where the solvent is nominally non-aqueous. We explore C—N coupling of amines using protonated carboxylic acids as reagents (clearly counter-intuitive entities, given that neutral carboxylic acids are normally proton donors not acceptors). The addition/water elimination product, the substituted amide, is not our primary focus; rather we are most interested in systems in which the presence of an ortho amino group allows further reaction to give a cyclic benzimidazole.

Benzimidazoles are an important class of heterocyclic compounds due to their wide application as active pharmaceutical moieties. Albendazole, mebendazole, triclabendazole, droperidol and pimozide are examples of drugs containing a benzimidazole scaffold. These drugs are used to treat cancers and ulcers, as well as fungal, viral and parasitic infections. The parent compound also serves as a precursor for the synthesis of vitamin B12. Derivatives of benzimidazoles are used industrially as ultraviolet filters and pigments. Conventionally, benzimidazole synthesis requires heating 1,2-phenyldiamine (PDA) with concentrated carboxylic acid for hours at high temperature, followed by the addition of a strong Lewis base to obtain the product. Recently, aldehydes and alcohols have been used as additives to facilitate the bulk reaction. However, the reaction can be performed at a milder temperature by adding catalysts such as cobalt, palladium, copper and even boranes. Despite the use of a metal catalyst, the reaction generally takes 6 to 12 hours to accomplish. Reactions involving radical pathways under UV-radiation are faster but require a radical generator such as rose Bengal. Other strategies have included the use of microwave irradiation in presence of triphenyl phosphite. Nevertheless, in terms of sustainable synthesis, reactions that occur at ambient temperature and pressure are still needed.

Herein, we demonstrate a metal-free synthetic strategy in which the rate of the benzimidazole synthesis is accelerated and occurs under ambient conditions inside charged microdroplets during their brief time of flight in the open air either to a mass spectrometer or in scaled-up experiments (see below) to a droplet collector. These electrosprayed microdroplets behave like micro/nano-reactors which undergo rapid desolvation and coulombic fission while finally releasing unsolvated product ions into the mass spectrometer.

These microdroplet accelerated reactions can be performed under ambient conditions using nESI or, in larger volumes, using electrosonic spray ionization (ESSI). Levitated Leidenfrost droplets allow milligram quantities of compounds to be synthesized in times on the order of minutes. Here, we use mass spectral fragmentation patterns (MS/MS experiments) to identify reaction intermediates and products, supplemented by isotope labeling and pH dependence experiments.

Accelerated microdroplet C—N bond formation reactions may include amide bond formation (A. K. Badu-Tawiah, A. Li, F. P. M. Jjunju and R. G. Cooks, Angewandte Chemie International Edition, 2012, 51, 9417-9421), alkyl azide reaction with Girard T (M. Girod, E. Moyano, D. I. Campbell and R. G. Cooks, Chemical Science, 2011, 2, 501-510), Schiff base formation reaction (R. M. Bain, C. J. Pulliam, S. T. Ayrton, K. Bain and R. G. Cooks, Rapid Communications in Mass Spectrometry, 2016, 30, 1875-1878), Katritzky transformation (Z. Wei, M. Wleklinski, C. Ferreira and R. G. Cooks, Angew Chem Int Ed Engl, 2017, 56, 9386-9390; and X. Yan, R. Augusti, X. Li and R. G. Cooks, ChemPlusChem, 2013, 78, 1142-1148), imines (Z. Wei, X. Zhang, J. Wang, S. Zhang, X. Zhang and R. G. Cooks, Chemical Science, 2018, 9, 7779-7786), quinoxolines formation (A. Saidykhan, Y. Nazir, W. H. C. Martin, R. T. Gallagher and R. D. Bowen, European Journal of Mass Spectrometry, 2017, 24, 3-11), and synthesis of isoquinolines and substituted quinolones (S. Banerjee and R. N. Zare, Angewandte Chemie International Edition, 2015, 54, 14795-14799) from their parent aldehyde or ketone and an amine or hydrazine. Such condensation reactions can be performed with a high rate of acceleration using charged microdroplets generated by electrospray. In most of the cases, a product formation is observed in a positive mode electrospray ionization mass spectrum after spraying the reaction mixture containing aromatic or aliphatic aldehydes or ketones and an amine. The reaction mechanism utilizes the extraordinary conditions of charged microdroplets. The excess surface proton concentration of positively charged microdroplets seems to act as a superacid to perform acid-catalyzed condensation reaction in many of the aforementioned reactions. The content of each reference mentioned in this preceding paragraph is incorporated by reference herein in its entirety.

Scheme 1 represents the reaction conditions used in conventional and microdroplet synthesis.

Conventional Methods

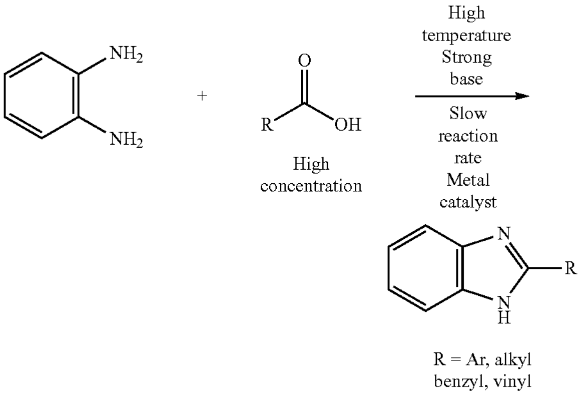

Microdroplet synthesis

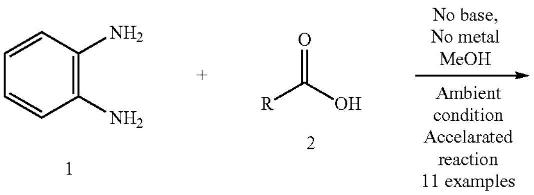

1 2

-continued

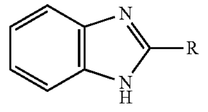

3

The droplet reaction was performed by electrospraying a 1.1 molar ratio of o-aryl diamine and carboxylic acid at 2-2.5 kV applied potential using nESI emitters of 5 μm tip diameter. The solvent was methanol and the concentration of each reactant 8 mM. Collision-induced dissociation (CID) with He as collision gas was used to record MS/MS spectra to characterize the products and intermediates. The scope of the microdroplet synthesis was assessed using seven diamines 1,2-phenyldiamine (PDA), 4-methyl-1,2-phenyldiamine, 4,5-dimethyl-1,2-phenyldiamine, 4-nitro-1,2-phenyldiamine, 4-chloro-1,2-phenyldiamine, 4-methoxy-1,2-phenyldiamine, 1,2-diaminonapthalene) and five carboxylic acids (formic acid (FA), acetic acid (AA), trifluoroacetic acid (TFAA), propanoic acid (PA) and benzoic acid (BA)).

Figure 3:
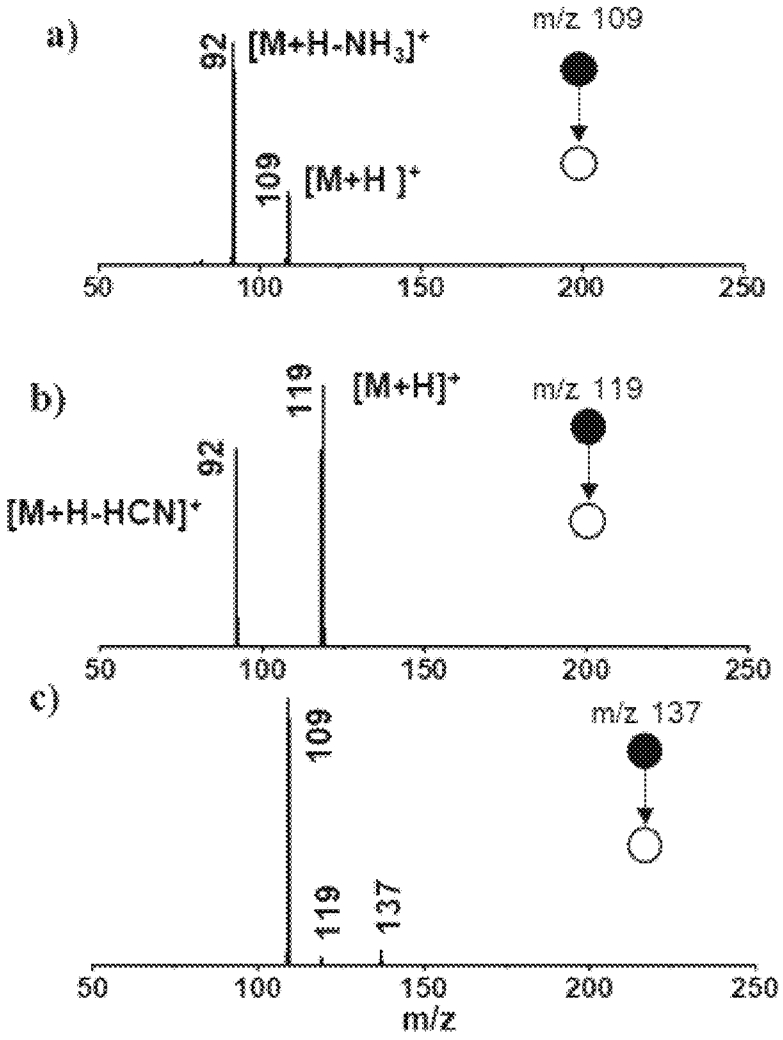
FIG. 3 panels A-C show MS/MS spectra of Panel A) reagent peak at m/z 109, Panel B) product peak at m/z 119, and Panel C) intermediate peak at m/z 137 for nESI microdroplet synthesis.
Figure 4:
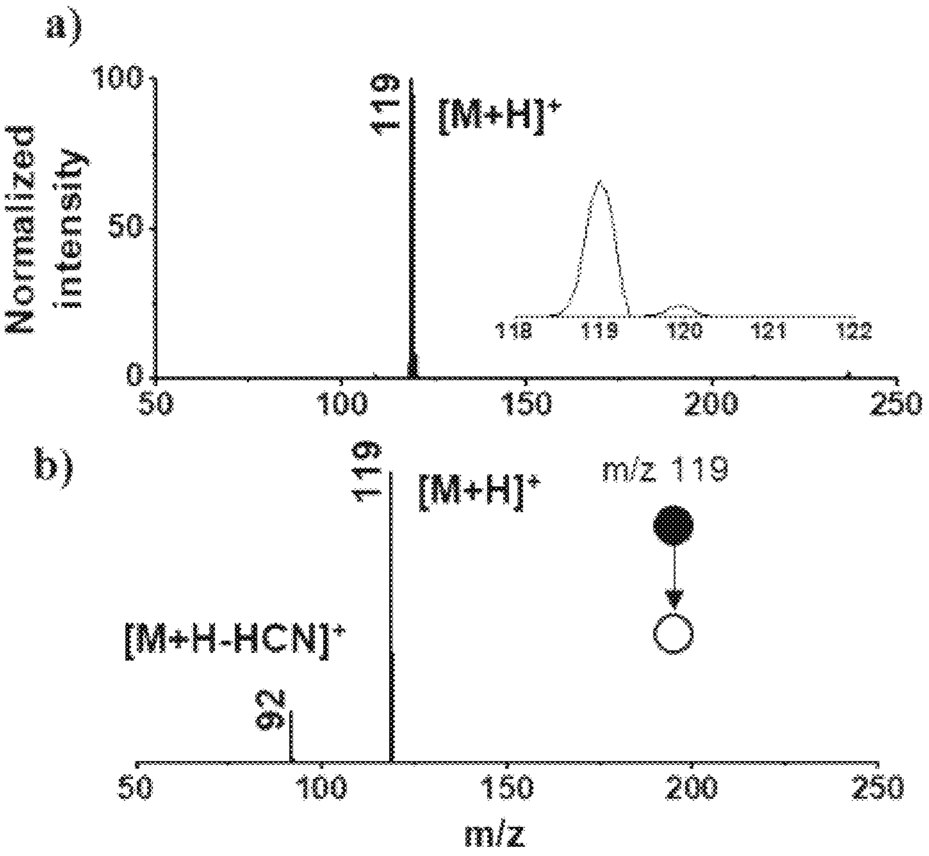
FIG. 4 panels A-B show mass spectra of standard benzimidazole. Panel A) mass spectrum of 1 mM solution of benzimidazole in methanol. Inset shows the isotopic distribution of the peak. Panel B) MS/MS spectrum of protonated benzimidazole at m/z 119.

FIG. 1 panels A-B compare the mass spectrum of PDA recorded with and without addition of formic acid. There is no benzimidazole product without the acid, the only signal being that at m/z 109 corresponding to protonated PDA. The inset of FIG. 1 panel A schematically illustrates the procedure used for microdroplet synthesis. The MS/MS spectrum of the ion at m/z 109 shows a characteristic neutral loss of ammonia (FIG. 3 panel A) confirming that the peak corresponds to protonated PDA. The ion at m/z 119 observed when the reaction mixture was electrosprayed fragmented by loss of a HCN molecule during CID (FIG. 3 panel B). This strongly suggests that the ion corresponds to protonated benzimidazole formed as a result of the reaction between PDA and FA. We verified this assignment by comparison with the MS/MS spectrum of the standard compound (FIG. 4 panels A-B). In addition to the product, m/z 119, the mass spectrum of the reaction mixture shows a peak at m/z 137 which corresponds to a hydrated intermediate. This ion might be the formamide or its cyclized form (i.e. 2c in acyclic or cyclized form, each including two tautomers). The mass-selected ion dissociates under CID to give a major peak at m/z 109 and a minor peak at m/z 119 (FIG. 3 panel C) consistent with both the formamide (which fragments back to starting material) and with the cyclic product (which undergoes dehydration to the benzimidazole).

Figure 5:
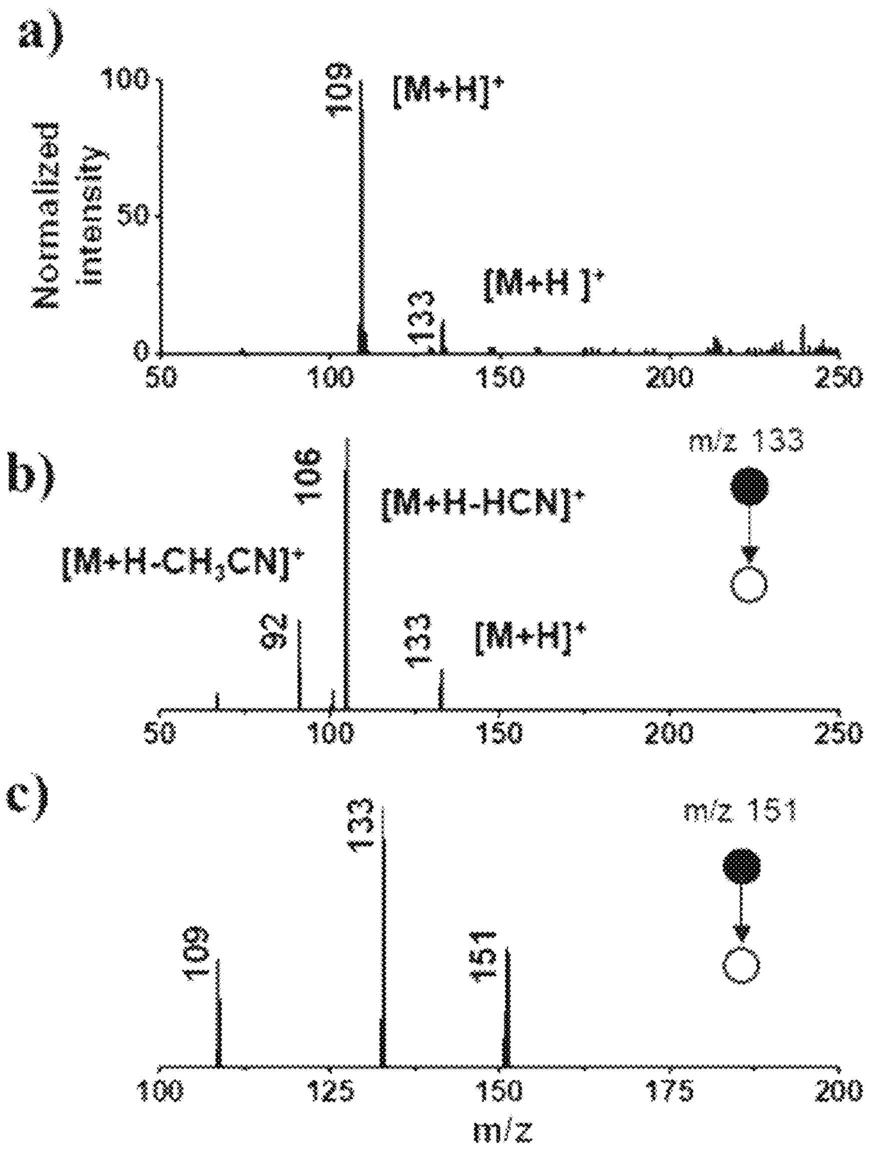
FIG. 5 panels A-C show microdroplet synthesis of 2-methylbenzimidazole. Panel A) Mass spectrum of the reaction mixture containing phenylenediamine (PDA) and acetic acid in methanol. The final concentration of the individual reagents is 8 mM. Panel B) MS/MS spectrum of the product at m/z 133 Panel C) MS/MS spectrum of intermediate at m/z 151.
Figure 6:
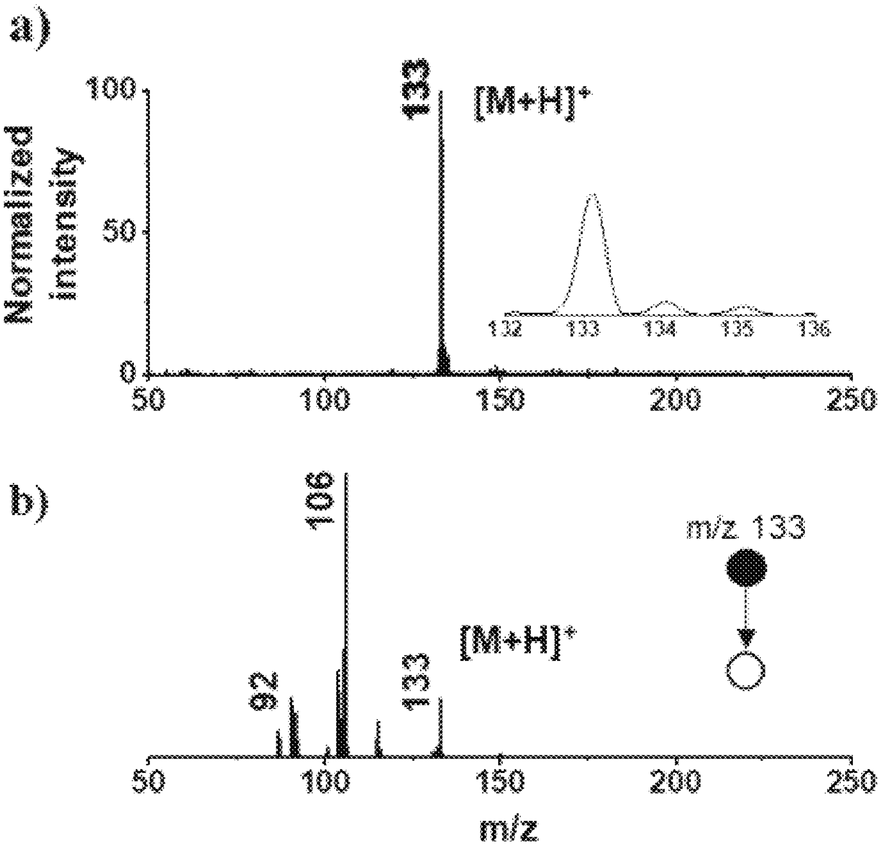
FIG. 6 panels A-B show mass spectra of standard 2-methylbenzimidazole. Panel A) Mass spectrum of 1 mM solution of 2-methylbenzimidazole in methanol. Inset shows the isotopic distribution of Panel B) MS/MS spectrum of the protonated 2-methylbenzimidazole at m/z 133.

A similar electrospray reaction was conducted between PDA and AA. This reaction produces 2-methylbenzimidazole, seen as the protonated form at m/z 133 in the full mass spectrum (FIG. 5 panel A), and confirmed by comparison of its MS/MS spectrum (FIG. 5 panel B) with that of the standard compound (FIG. 6 panels A-B). The peak at m/z 151 in the full mass spectrum is assigned to the formation of the corresponding intermediate amide. Fragmentation of this ion shows a major peak at m/z 109, which corresponds to the starting reagent and most significantly, neutral loss of a water molecule to form the reaction product at m/z 133 (FIG. 5 panel C).

Figure 7:
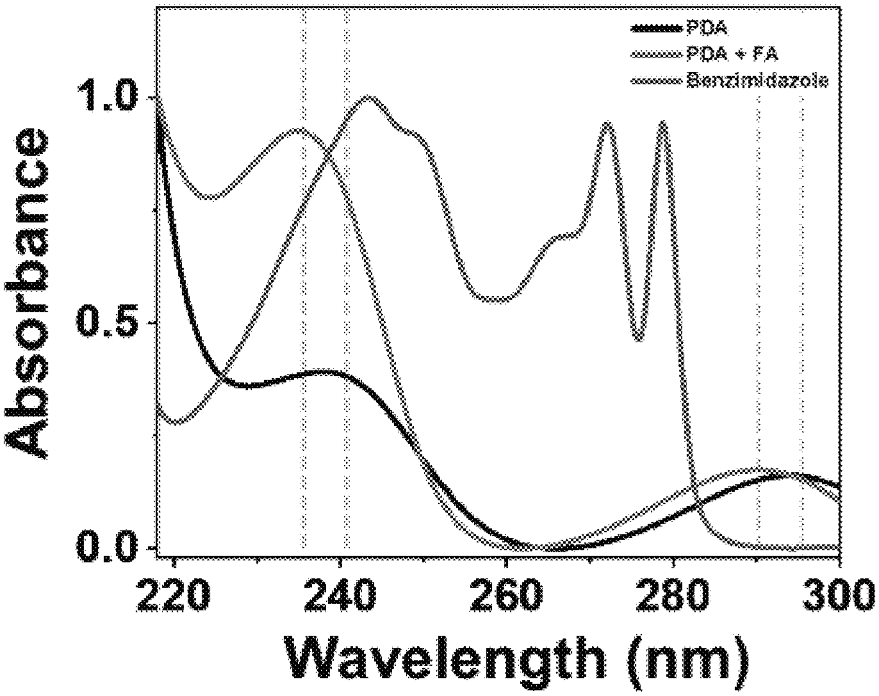
FIG. 7 shows UV-vis spectra of o-phenylenediamine (black), reaction mixture for the synthesis of benzimidazole (red) and standard product (blue). The shift in the UV-vis spectra, as indicated by dotted lines, is due to the addition of the formic acid and correspond to Brønsted acid formation in solution by addition of a proton.
Figure 8:
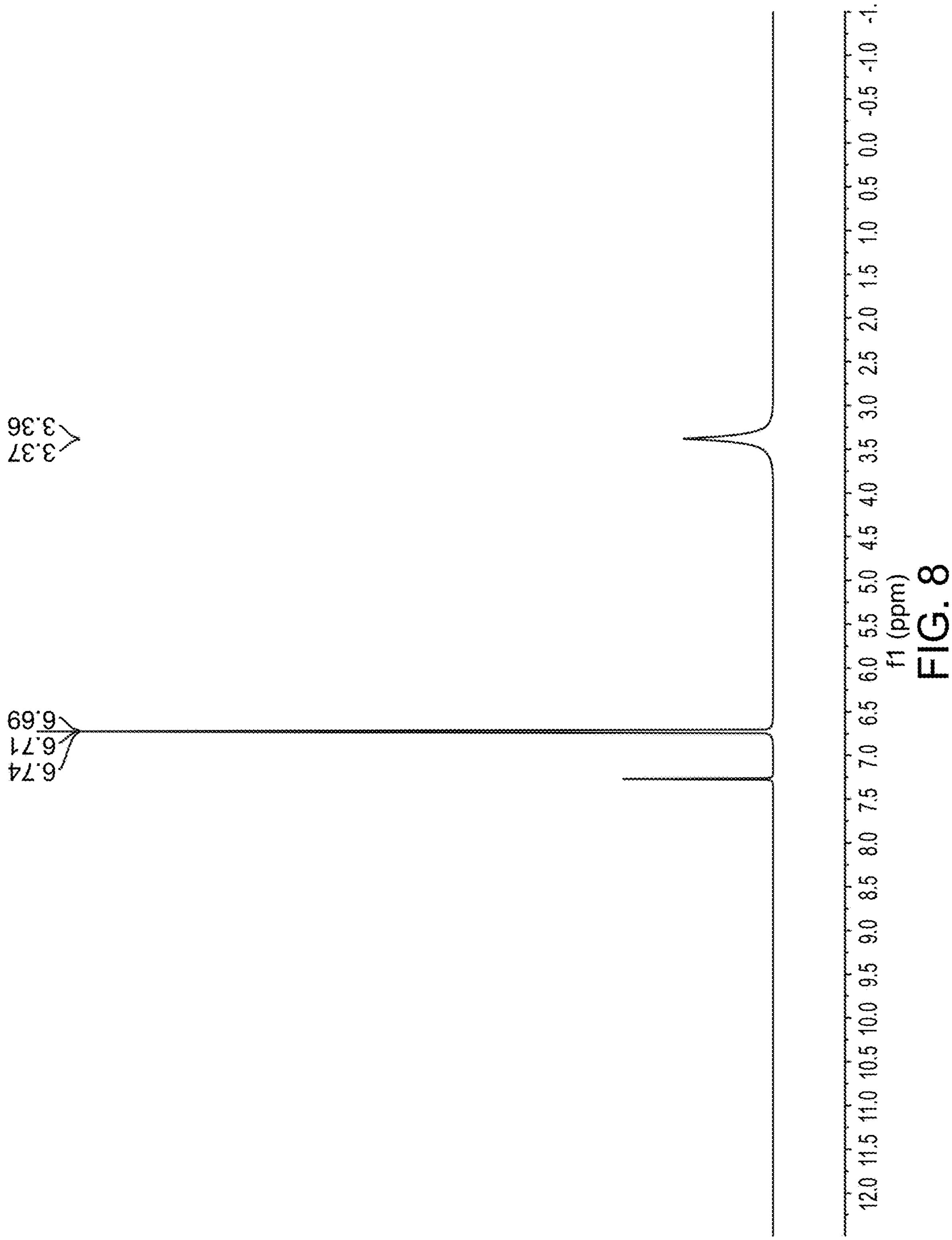
FIG. 8 is 1H NMR data for o-phenylenediamine in CDCl3.1H NMR (400 MHz, CDCl3) δ 6.71 (s, 1H), 3.49-3.23 (m, 1H). Solvent peak is observed at 7.26 ppm.
Figure 9:
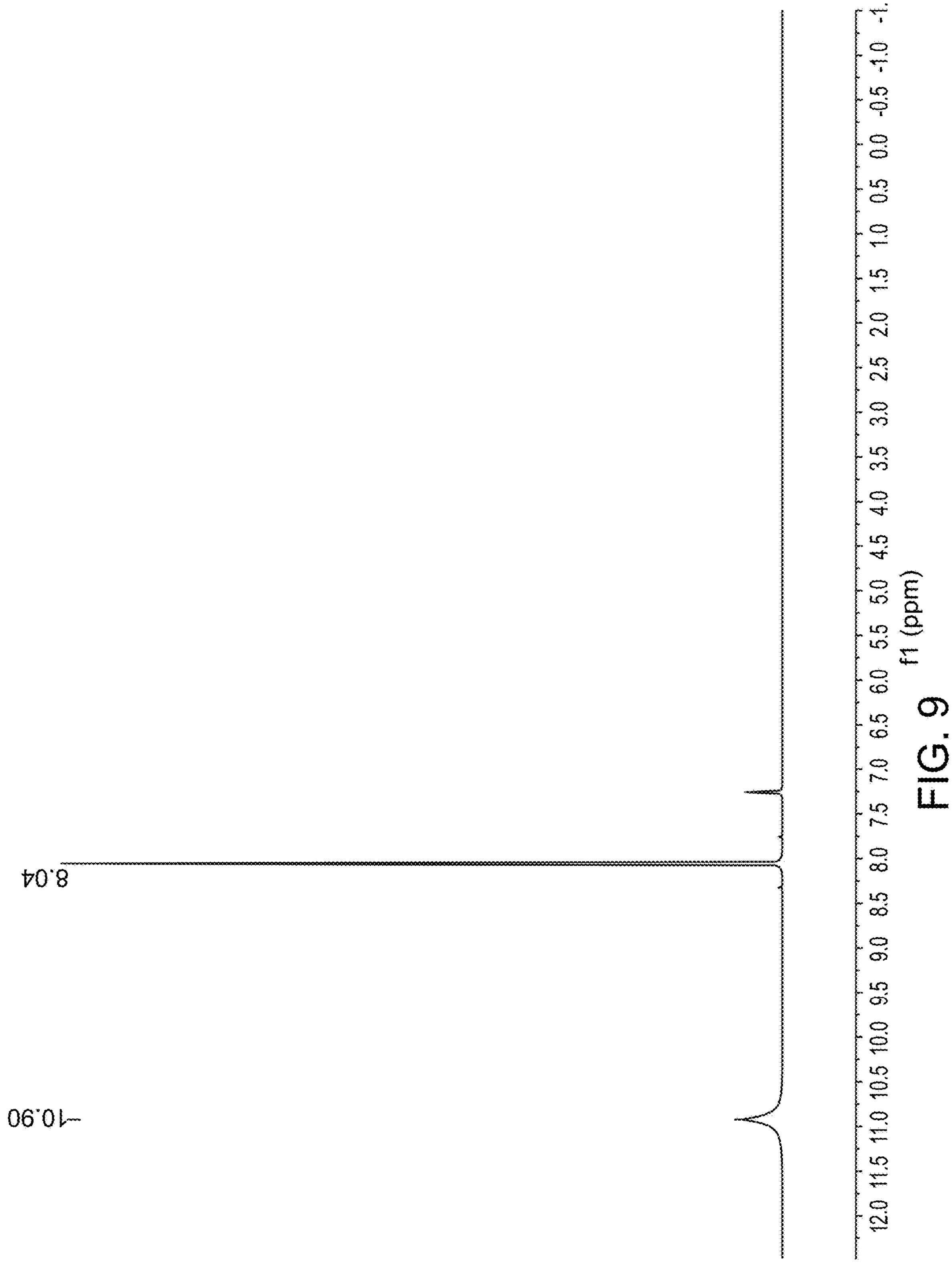
FIG. 9 is 1H NMR data for formic acid. 1H NMR (400 MHz, CDCl3) δ 10.90 (s, 1H), 8.04 (s, 1H). Solvent peak is observed at 7.26 ppm.
Figure 10:
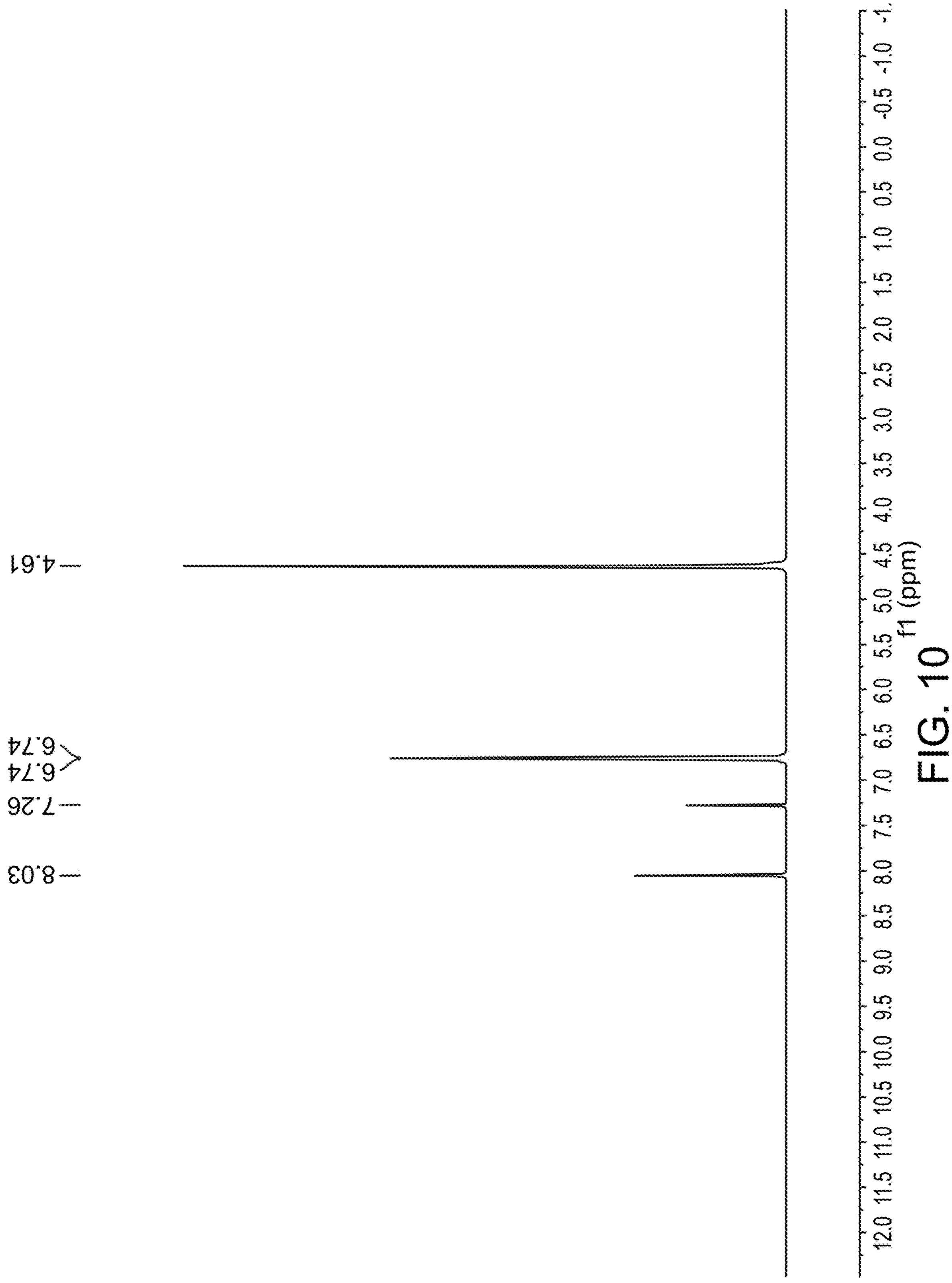
FIG. 10 is 1H NMR data for a mixture of o-phenylenediamine and formic acid. 1H NMR (400 MHz, CDCl3) δ 8.02 (s, 1H), 6.79-6.69 (m, 5H), 4.61 (s, 7H). Solvent peak is observed at 7.26 ppm.
Figure 11:
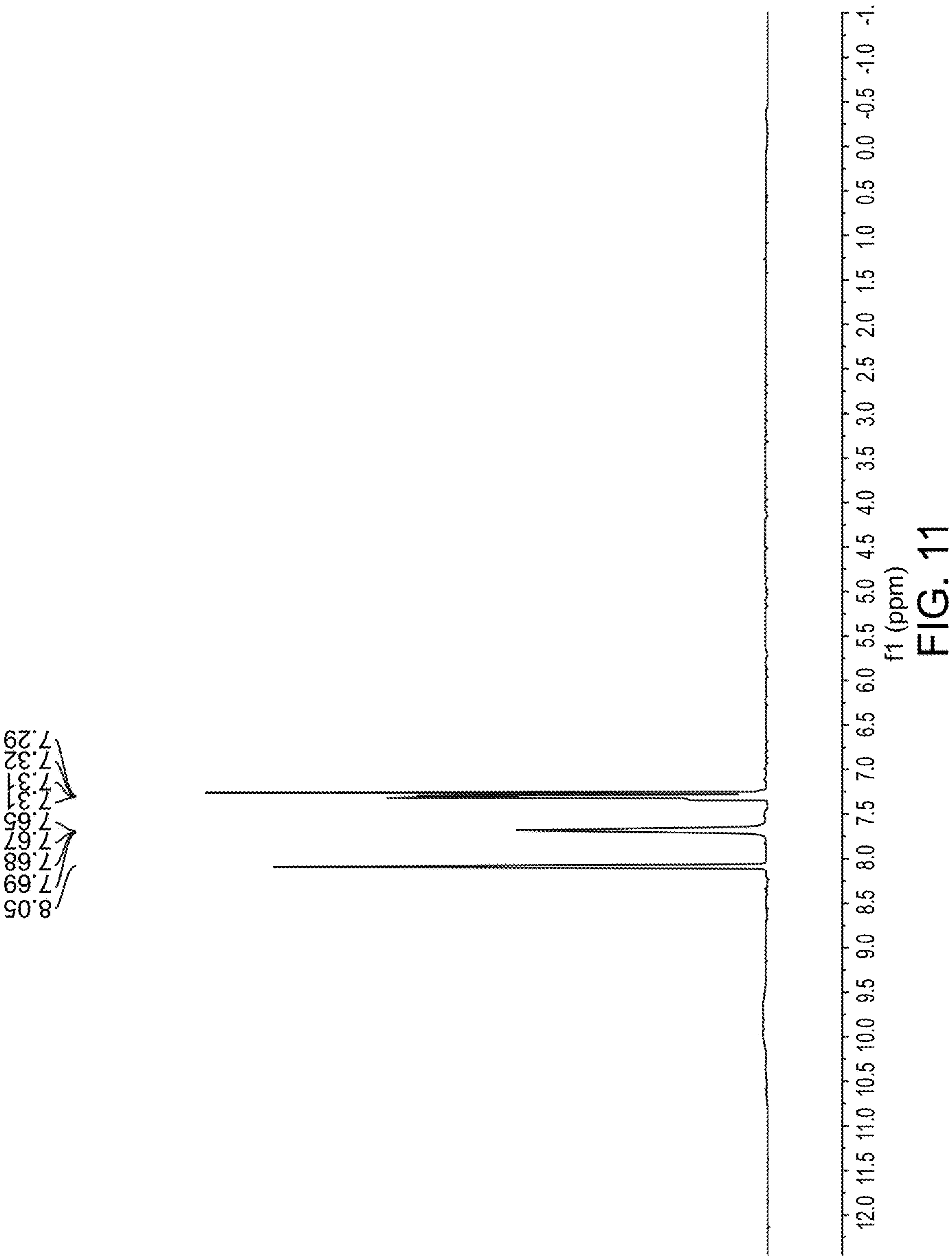
FIG. 11 is 1H NMR data for standard benzimidazole. 1H NMR (400 MHz, CDCl3) δ 8.08 (s, 1H), 7.71-7.64 (m, 2H), 7.31 (dt, J=6.1, 3.6 Hz, 2H). Solvent peak is observed at 7.26 ppm.
Figure 12:
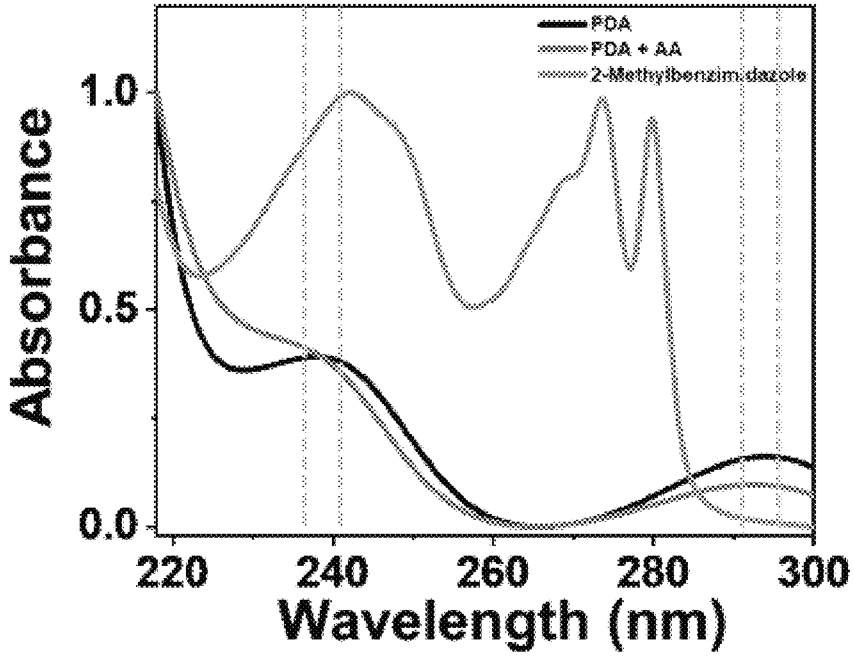
FIG. 12 is UV-vis spectra of o-phenylenediamine (black), its mixture with acetic acid (green) and standard 2-methylbenzimidazole (violet).
Figure 13:
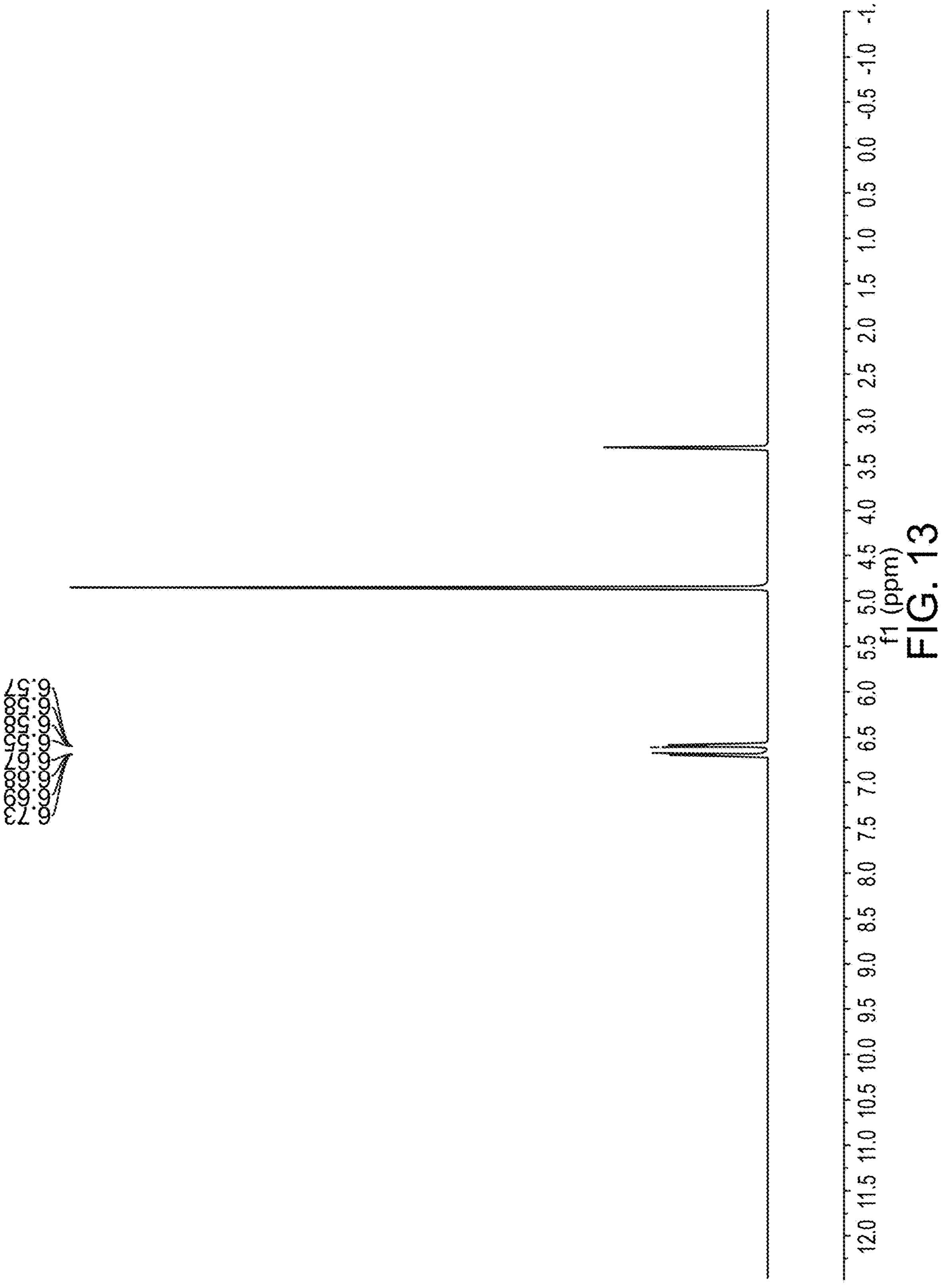
FIG. 13 is 1H NMR data for standard o-phenylenediamine. 1H NMR (400 MHz, MeOD) δ 6.69 (dd, J=5.7, 3.5 Hz, 1H), 6.58 (dd, J=5.8, 3.4 Hz, 1H).
Figure 14:
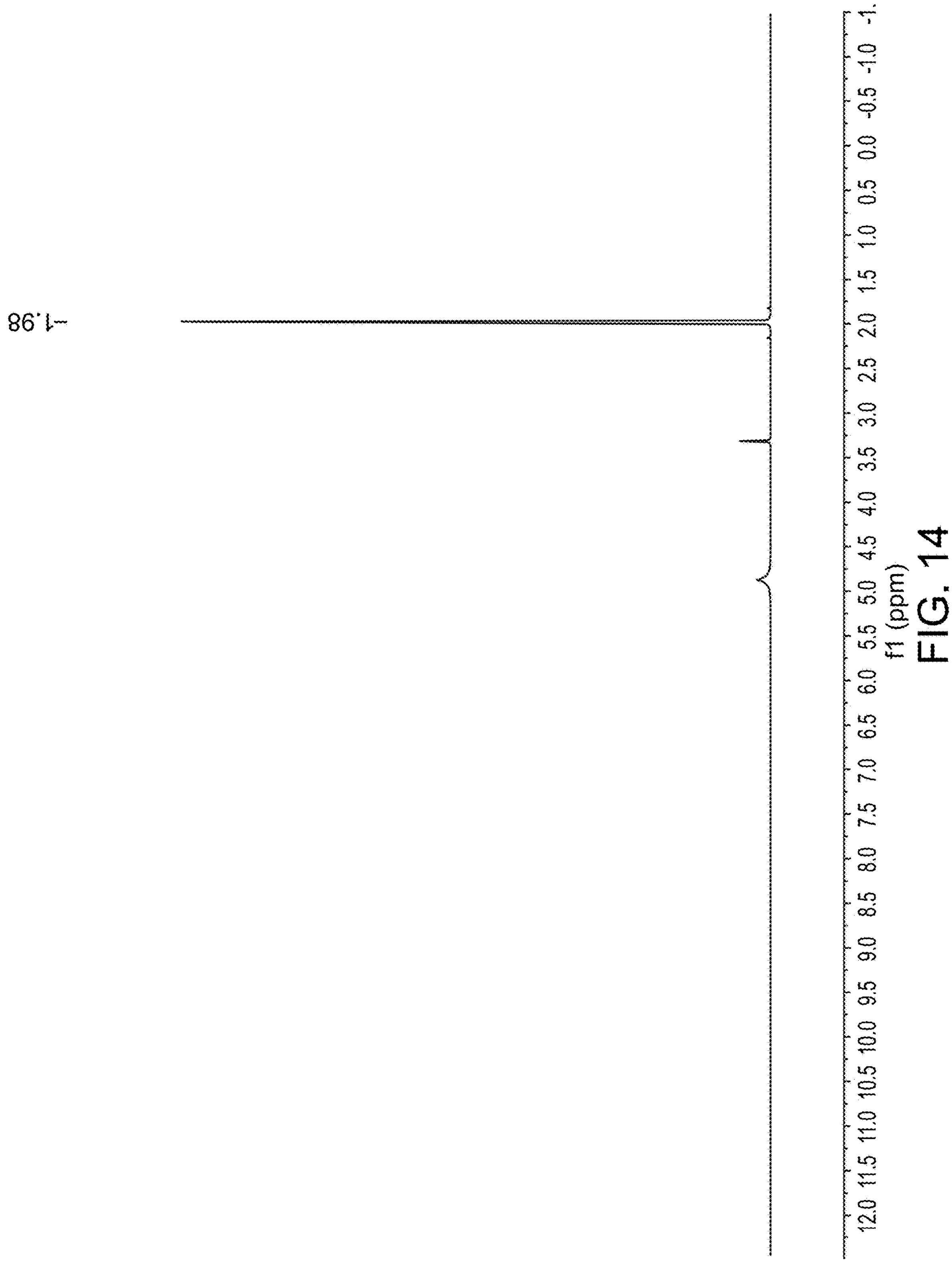
FIG. 14 is 1H NMR data for acetic acid. 1H NMR (400 MHz, MeOD) δ 1.98 (s, 1H). Peaks at 4.85 ppm and 3.30 ppm are solvent peaks.

To confirm that these reactions do not occur upon immediate mixing of the reagents in methanol, UV-vis and 1H NMR spectra of the authentic products and the reaction mixtures of the benzimidazole and 2-methylbenzimidazole synthesis were obtained. 1H NMR experiments were performed in deuterated chloroform for benzimidazole and its reaction mixture while deuterated methanol was used for 2-methylbenzimidazole and its reaction mixture. The mixtures of reagents were kept for 10 minutes at room temperature before recording the spectra. The UV-vis spectra of the PDA/FA mixture (FIG. 7) show a shift in the PDA spectrum upon the addition of formic acid, which protonates the amine. However, the spectral signatures corresponding to the product were not observed in the UV-vis spectrum of the reaction mixture or in the 1H NMR spectra of these solutions (FIGS. 8-11). Analogous results were obtained for the reaction between PDA and AA (FIGS. 12-16). These results confirm that the reagents do not react in bulk.

Initial estimates of the yield of the microdroplet synthesis reactions were obtained using the measured conversion ratio (CR), the ratio of the intensity between the product (P) and the sum of the intensities of the starting material (SM) and product, viz., [P]/([SM]+[P]). Note that this estimate does not correct for differences in ionization energy and that more accurate yields were obtained by collecting and purifying product (see below). The conversion ratios for the benzimidazole and 2-methylbenzimidazole syntheses were 30% and 11%, respectively (with MS inlet capillary temperature at 50° C.). This difference in the conversion ratio is surprisingly large but consistent with the expected lower electrophilicity of the methyl substituted carbon in AA vs. the unsubstituted carbon of FA. We noticed a change in the conversion ratios as a function of the mass spectrometer inlet capillary temperature as now discussed.

Temperature and Solvent Effects

Figure 2:
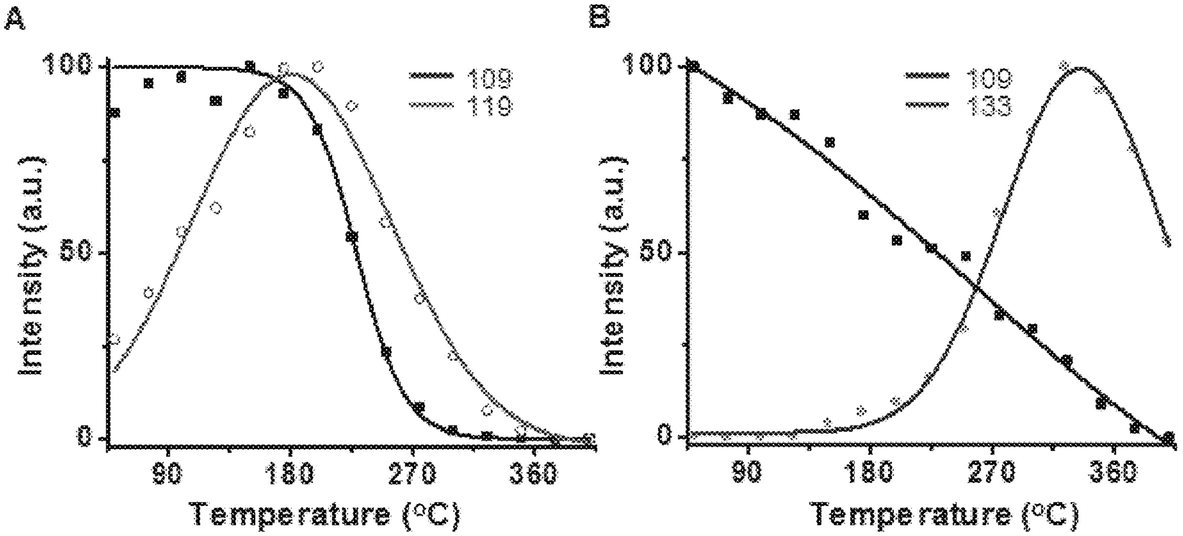
FIG. 2 panels A-B show effect of inlet temperature of the mass spectrometer on product ion intensity showing (Panel A) protonated reagent (black) and product (red) for the synthesis of benzimidazole and (Panel B) reagent (black) and product (blue) for synthesis of 2-methybenzimidazole. The temperature was varied from 50 to 400° C. for both reactions.
Figure 15:
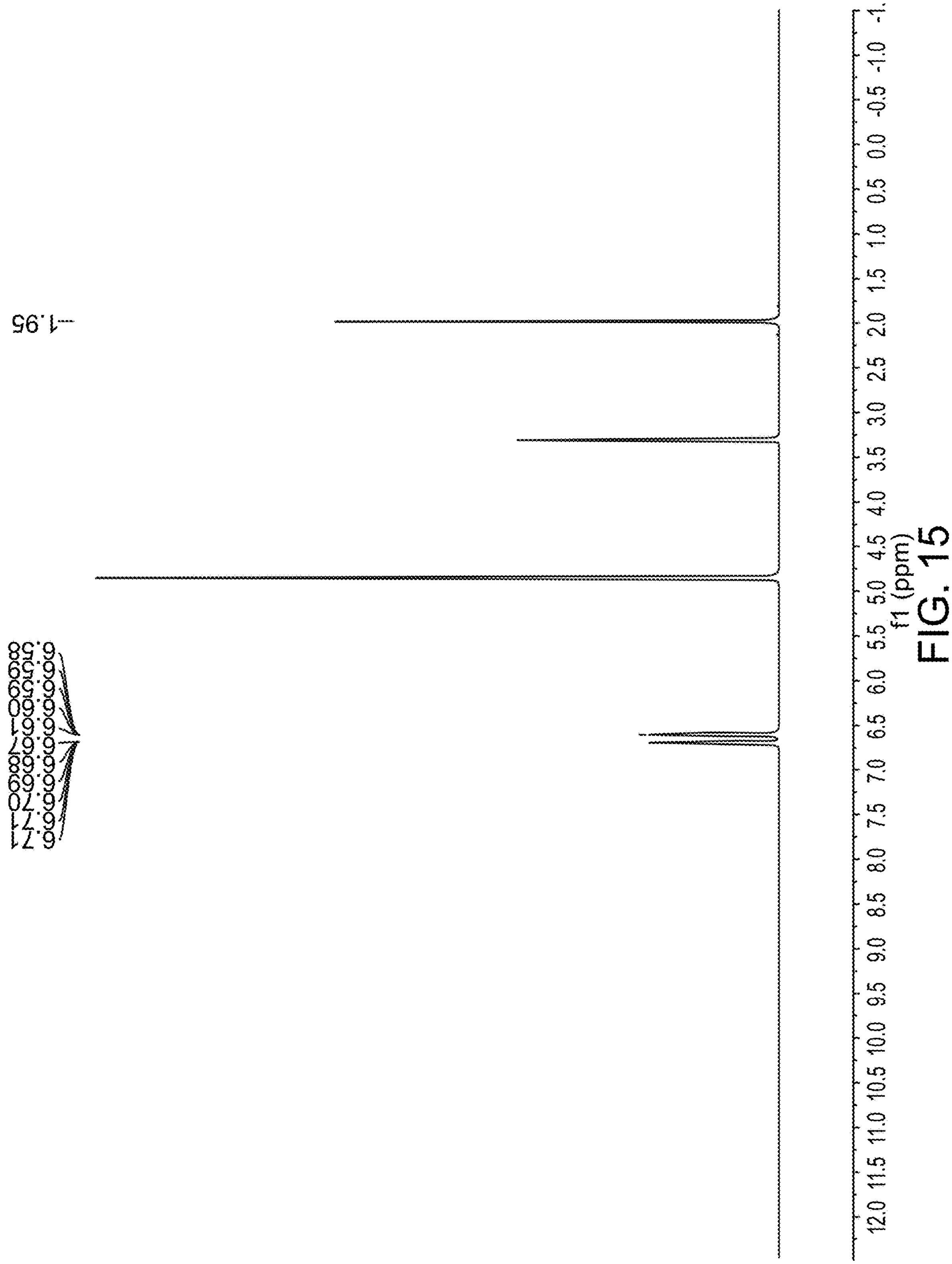
FIG. 15 is 1H NMR data for mixture of o-phenylenediamine and acetic acid. 1H NMR (400 MHz, MeOD) δ 6.69 (dq, J=6.4, 3.6, 3.0 Hz, 1H), 6.59 (dt, J=5.8, 2.8 Hz, 1H), 1.98 (s, 1H). Peaks at 4.85 ppm and 3.30 ppm are due to solvent.
Figure 16:
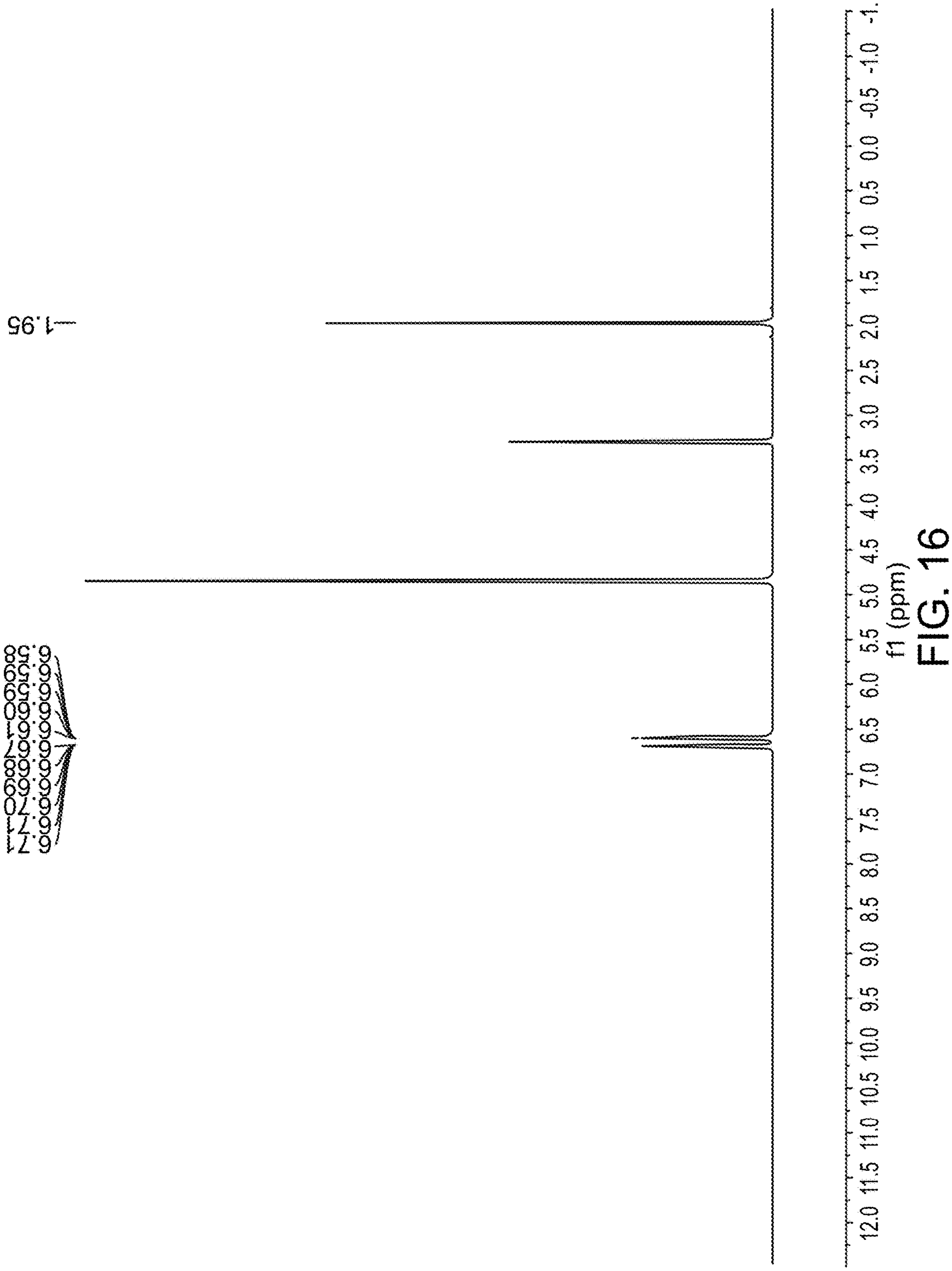
FIG. 16 is 1H NMR data for standard 2-methylbenzimidazole. 1H NMR (400 MHz, MeOD) δ 7.51-7.37 (m, 1H), 7.16 (dd, J=6.0, 3.2 Hz, 1H), 2.55 (s, 2H). Peaks at 4.85 ppm and 3.30 ppm are due to solvent.
Figure 17:
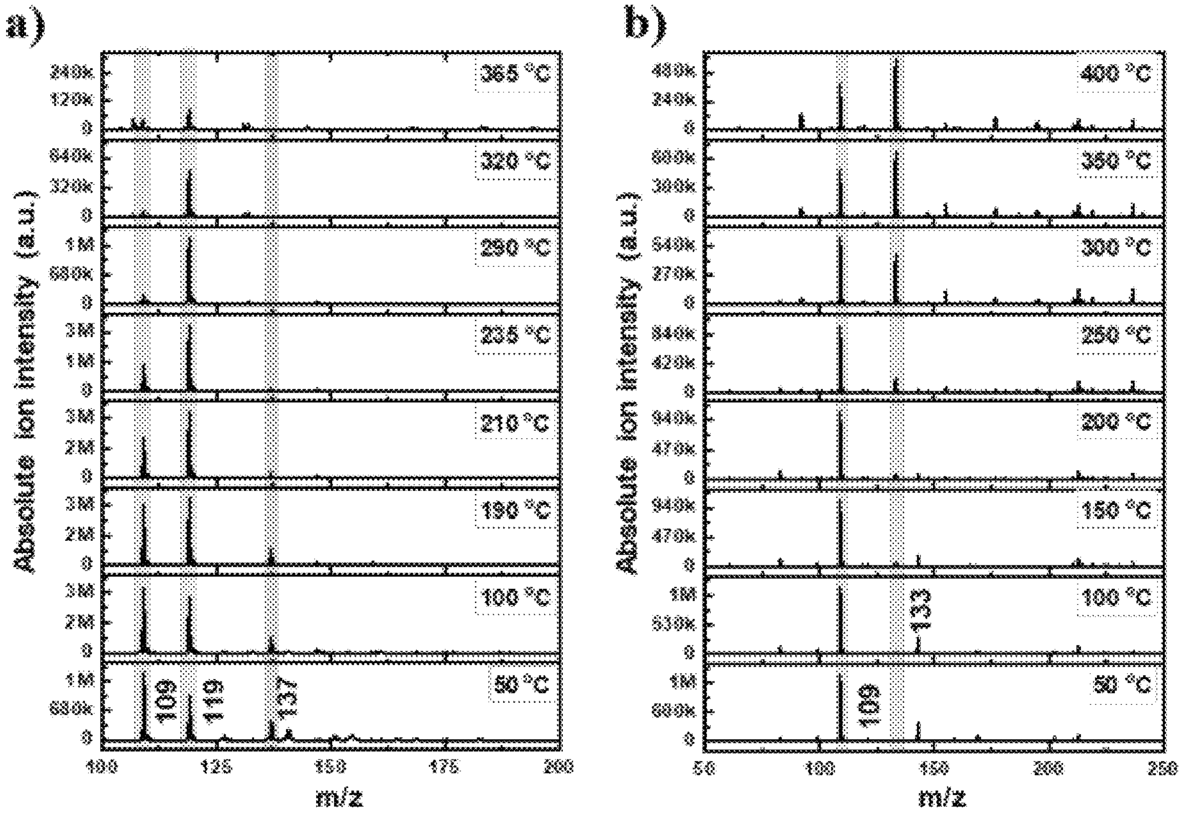
FIG. 17 panels A-B show temperature dependent mass spectra for microdroplet synthesis of Panel A) benzimidazole and Panel B) 2-methylbenzimidazole. The reagent peak at m/z 109, as indicated by yellow shading, decreases with increasing temperature, whereas, the product peak at m/z 119, m/z 133, as indicated by green shading, increases with increasing temperature.

Studies of the Pomeranz-Fritsch and the Combes reactions showed that temperature of the MS inlet plays an important role, with an increase in inlet temperatures having opposite effects on the rate of these two reactions. In the benzimidazole synthesis, a significant increase in the product yield was observed by increasing the inlet temperature. Both the FA and the AA reactions showed maximum conversion ratios at higher, albeit different, temperatures (FIG. 2 panels A-B). In the case of PDA/FA a maximum was observed at 200° C. while for PDA/AA the maximum was reached at 350° C. It was also noted in both cases, that the intensity of the intermediate peak decreases and almost disappears as the temperature is raised to 200° C. Mass spectra of the reaction mixtures for the benzimidazole and 2-methylbenzimidazole syntheses at eight different temperatures ranging from 50 to 400° C. are shown in FIG. 15 panels A-B. Based on the temperature dependence for PDA/FA (FIG. 15 panel A) the relative abundance of the product peak at m/z 119 increases from 50 to 180° C. and become a base peak at 200° C. decreasing beyond this point. For PDA/AA shows a similar trend but over a higher temperature range (270 to 400° C.) and with sharper increase in product signal, m/z 133 (FIG. 15 panel B).

The temperature data suggest that removal of water helps shift the dehydration/rehydration equilibrium to favor product formation. Although the effect of temperature is expected to be different for the different reactions because of their different energy requirements, the large difference between the product peak maxima (180° C. for benzimidazole but 350° C. for 2-methyl benzimidazole) is noteworthy.

Mechanism

Scheme 2 below provides a proposed mechanism for the acid-catalysed benzimidazole synthesis in charged microdroplets. A similar mechanism can be written starting from the more stable carbonyl protonated form of the acid.

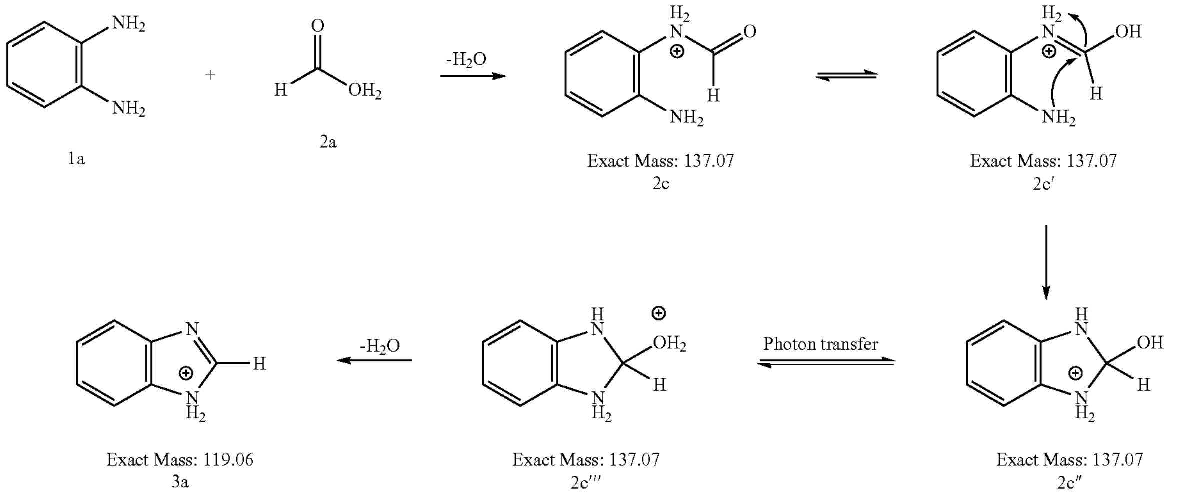

1a 2a 2c 2c' 3a 2c''' 2c''

Based on the above data, we speculate that the reaction must go through an acid catalyzed pathway, but not one driven by protonation of the amine. It is known that proton concentrations at the surface of positively charged electrosprayed aqueous droplets is much higher than in the bulk. So we believe, without being limited by any mechanism of action, that a very high proton concentration at the surface of a droplet containing water will protonate neutral formic acid to create the electrophilic carbon (2a) which is subject to nucleophilic attack by the lone pair of the amine. Subsequent loss of water results in the formation of a formamide intermediate (2c). Intramolecular nucleophilic attack at the carbon in the enol form of the intermediate (2c') by the lone pair of the adjacent nitrogen results in formation of the five-membered ring intermediate (2c"). Finally, dehydration of its tautomer (2c''') leads to protonated benzimidazole (3a) as final product. The intermediates 2c, 2c', 2c" and 2c''' are indistinguishable by mass/charge ratio, all occurring at m/z 137 (FIG. 1*i*). The MS/MS spectrum of m/z 137 (FIG. 3 panel C) shows that this ion can either fragment back to PDA (m/z 109) by loss of a CO molecule or lose water to form the benzimidazole product (m/z 119). These two processes give us confidence in the fact that the ion m/z 137 encompasses several isomers, as illustrated in Scheme 2. An analogous intermediate, m/z 151, is noted for the PDA/AA reaction and its fragmentation pattern (FIG. 5 panel B) confirms this.

Figure 18:
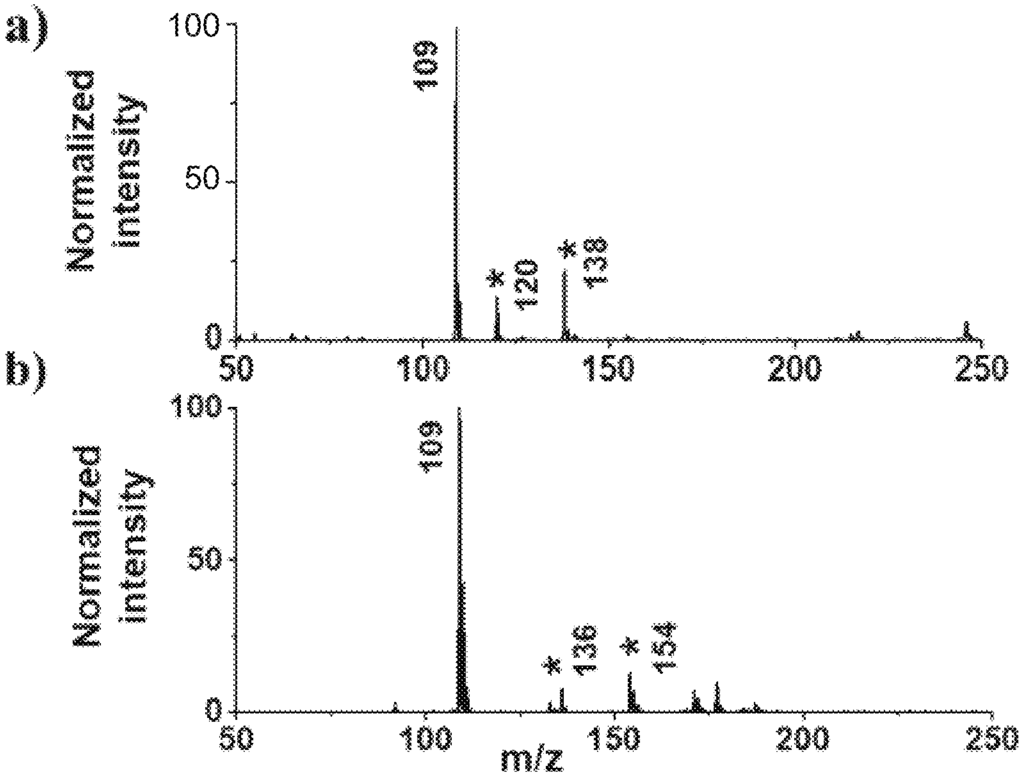
FIG. 18 panels A-B show isotope labeling experiments. Mass spectra showing reaction mixture for microdroplet reaction with PDA of deuterated Panel A) formic acid (DCOOH) and Panel B) acetic acid (CD3COOH). The isotopically labeled product peaks are indicated with stars. The solvent used for the reaction is deuterated methanol. The temperature of the inlet was set to 50° C. for these experiments.

The mechanism illustrated in Scheme 2 was also tested using formic-d acid (DCOOH). We expected isotopically labeled intermediates and product according to the proposed reaction pathway and observed the deuterated benzimidazole at m/z 120 and the deuterated intermediate at m/z 138 (FIG. 18 panel A). Fragmentation of the m/z 138 peak gives protonated reagent as well as the deuterated product at m/z 109 and 120. Analogously, isotopically labeled 2-methylbenzimidazole at m/z 136 and the intermediate at m/z 154 were observed with $CD_3COOH$ (FIG. 18 panel B). These results agree with expectations and support the suggestion that reaction occurs through a protonated carboxylic acid pathway.

Thin Film Reactions

Figure 19:
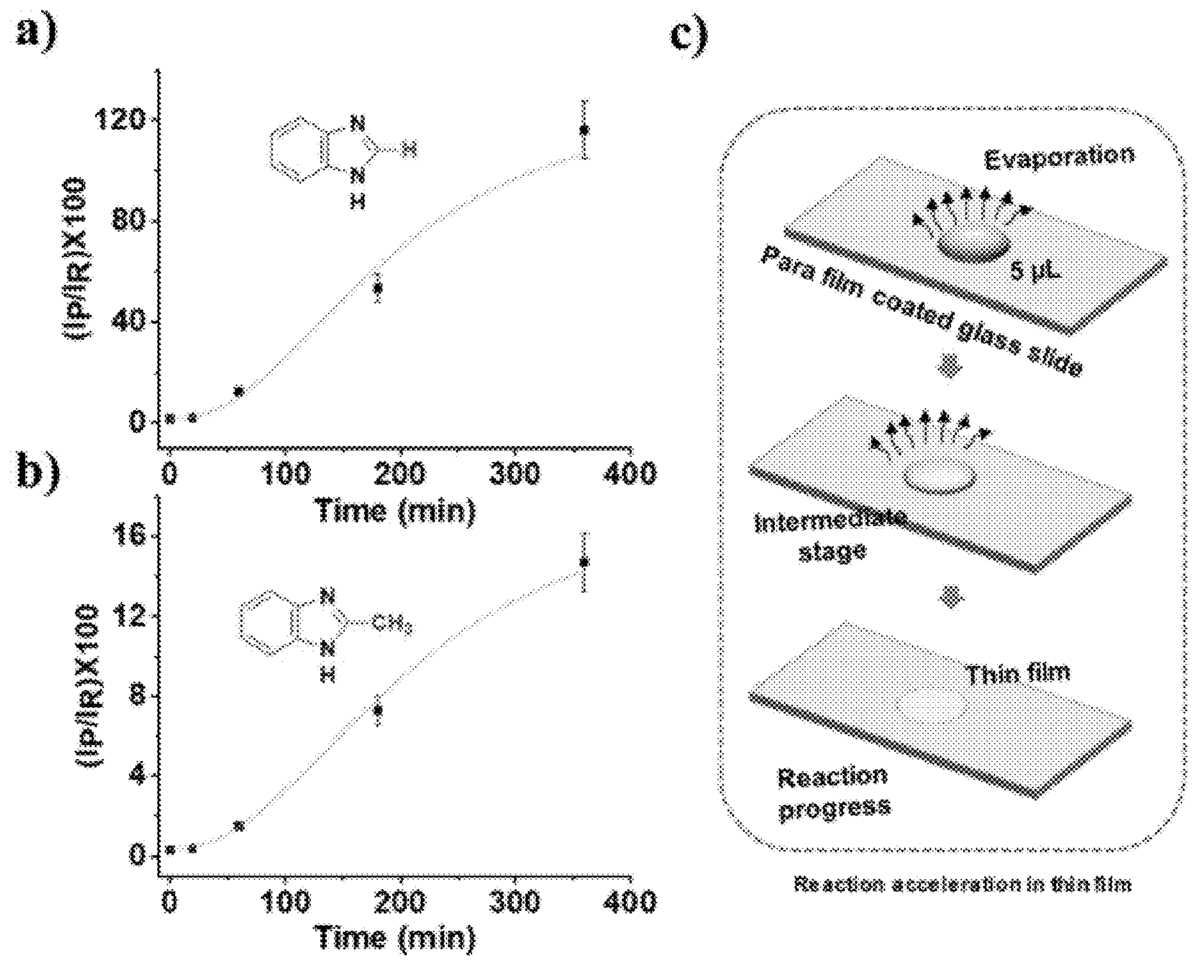
FIG. 19 panels A-C show product to reagent ion intensity ratio for ambient thin film reactions Panel A) benzimidazole and Panel B) 2-methylbenzimidazole synthesis. Panel C) Schematic illustration of the thin film experiments from Z. Wei, M. Wleklinski, C. Ferreira and R. G. Cooks, Angewandte Chemie International Edition, 2017, 56, 9386-9390.

Without being limited by any particular theory or mechanism of action, our view of the reaction mechanism is that droplets slowly evaporate and the very high acidity of the droplet surface allows protonation of the carboxylic acid followed by nucleophilic attack by the one amino group and by dehydration, before cyclization and a second dehydration event. It seems likely that the dehydration of the intermediate is the slow step in the reaction, hence the effect of the inlet temperature. If these arguments are correct, then it should be possible to observe the accelerated reaction entirely at ambient temperature (lowest inlet temperature was 50° C.). To test this claim, a thin film of reaction mixture in methanol was held at ambient temperature in the open lab. The mixture contained a trace (2.5 ppm) of the non-volatile acid, p-toluenesulfonic acid. This was done as a result of earlier ambient temperature accelerated thin film reactions in which traces of nonvolatile additives allowed continuous long-term reaction with elimination of water or other small molecules. The nonvolatile acid helps in creating and maintaining a micro/nano-thin film on the surface. Kinetic data were recorded (FIG. 19 panels A-C) to follow by MS benzimidazole and 2-methylbenzimidazole formation in this thin film experiment. In parallel with earlier studies on the base-catalyzed Katritsky transamination, we see that the reaction does not occur for an initial period of some minutes (during which methanol solvent is evaporating) but it then increases in rate before plateauing at 6 hours with 120% and 16% product-to-reagent peak intensity ratios for the benzimidazole and 2-methylbenzimidazole, respectively. Clearly, the reactions are accelerated in the thin film compared to bulk, and increasingly so as the film becomes thinner with continued methanol evaporation. However, the reaction rate is moderate in comparison to the ambient droplet phase synthesis (using EESI and discussed below) and small in comparison to the elevated temperature nESI microdroplet synthesis. The large differences in rate associated with simple methyl substitution are also replicated. These data support the conclusions on the reaction mechanism already outlined.

Figure 20:
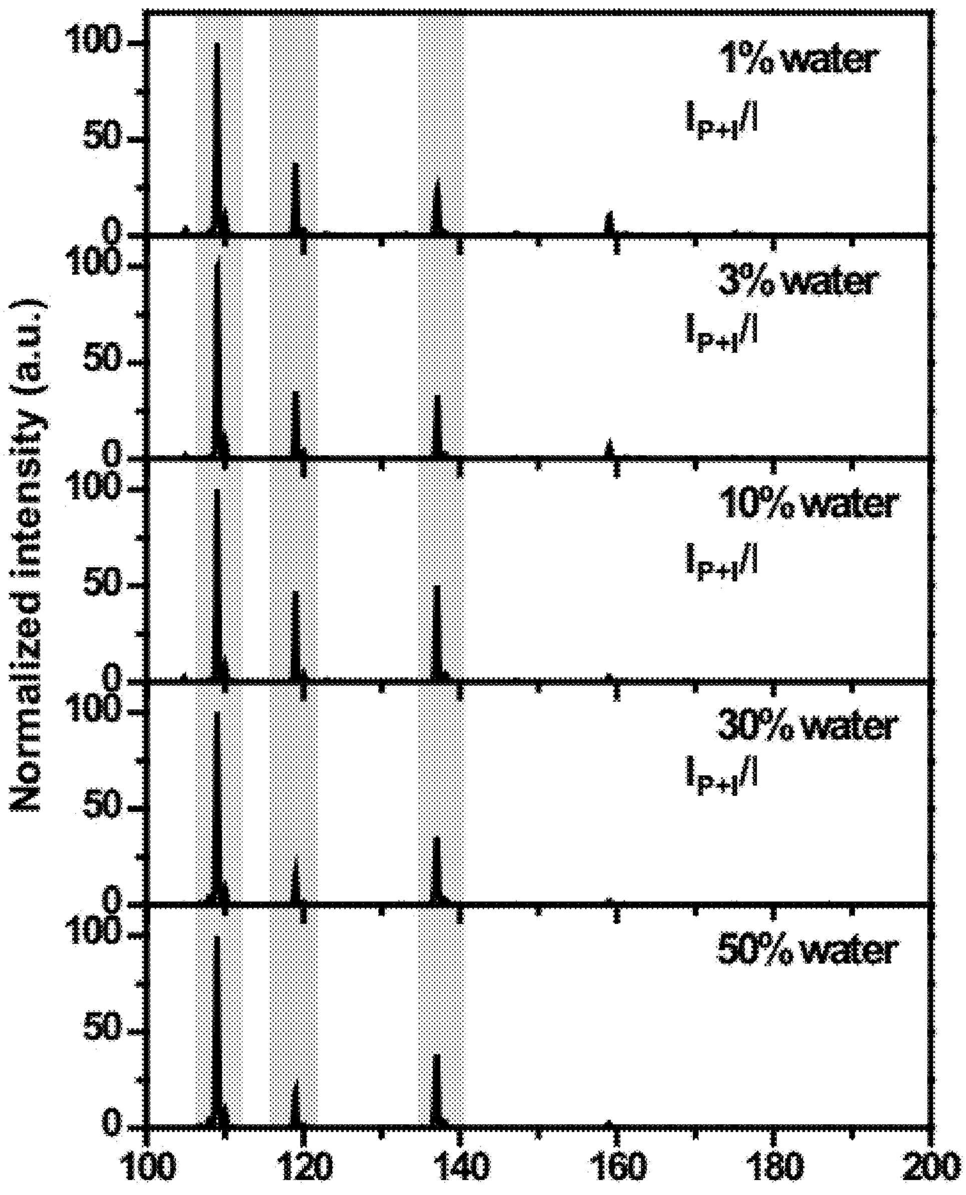
FIG. 20 shows benzimidazole reaction in presence of macroscopic amounts of water monitored by relative intensity of the product m/z 117 and the intermediate m/z 137. With increasing water concentration to 10%, we see increased product and intermediate formation. However, above this concentration the relative product and intermediate intensities fall.
Figure 21:
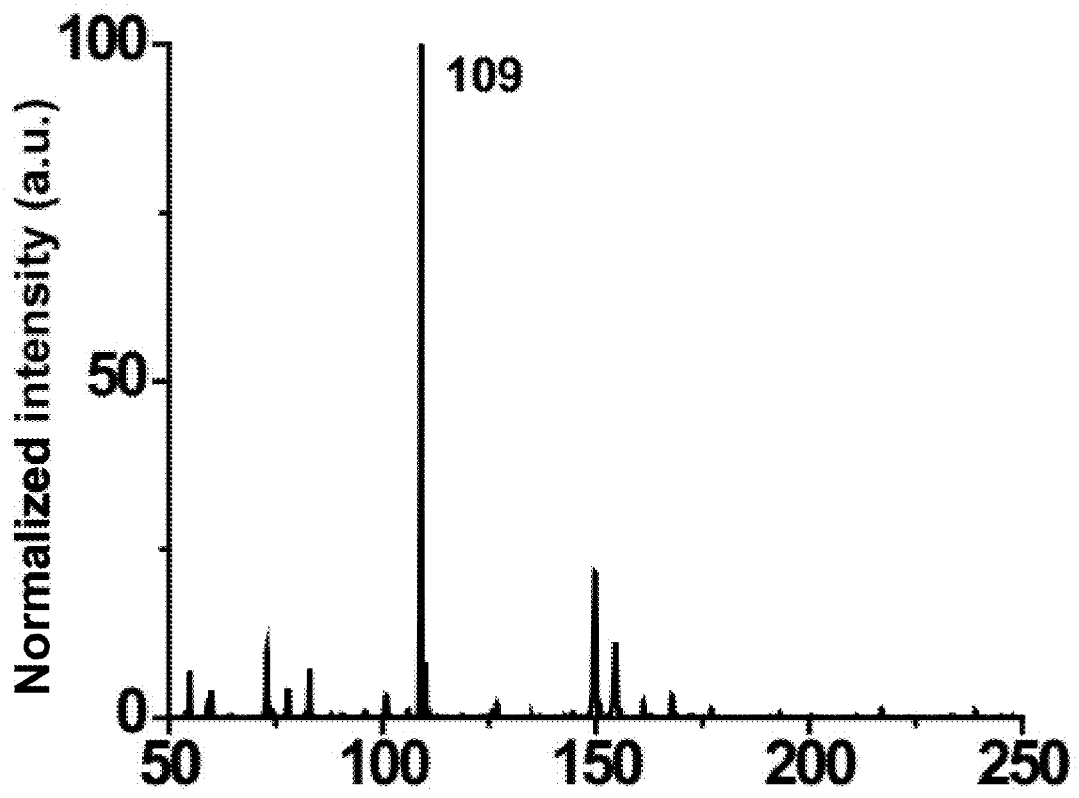
FIG. 21 shows benzimidazole reaction in dry ACN. Note the low signal (noise) and the absence of both product and intermediate ion signals. The other peaks seen in the mass spectrum are from the background.

The mechanistic arguments also need to include consideration of the solvent system, especially because we invoke a highly acidic environment at the droplet surface. Experiments done by varying the percentage of water in methanol over the range 1-50% showed that a low percentage of water (1-10%) favors the reaction (FIG. 20). The relative product plus intermediate ion intensity increasing from 62 to 95% over this range. However, at higher water concentrations the relative intensity of the product plus intermediate peaks decreases significantly to 52-54% and when the reaction is performed in dry ACN we observe no product at all (FIG. 21). These results are consistent with a balance between reagent solubility, methanol evaporation and formation of a super acid surface layer of water in the almost fully evaporated microdroplets. This clearly aligns with literature data on the high acidity of the surfaces of aqueous droplets while extending the concept of super acid formation in microdroplets to organic/aqueous mixed solvents. We imagine that water, being a stronger base than methanol, takes the charge and occupies the surface of a small methanol droplet thereby protonating neutral formic acid and driving the benzimidazole synthesis.

pH Dependence

Figure 22:
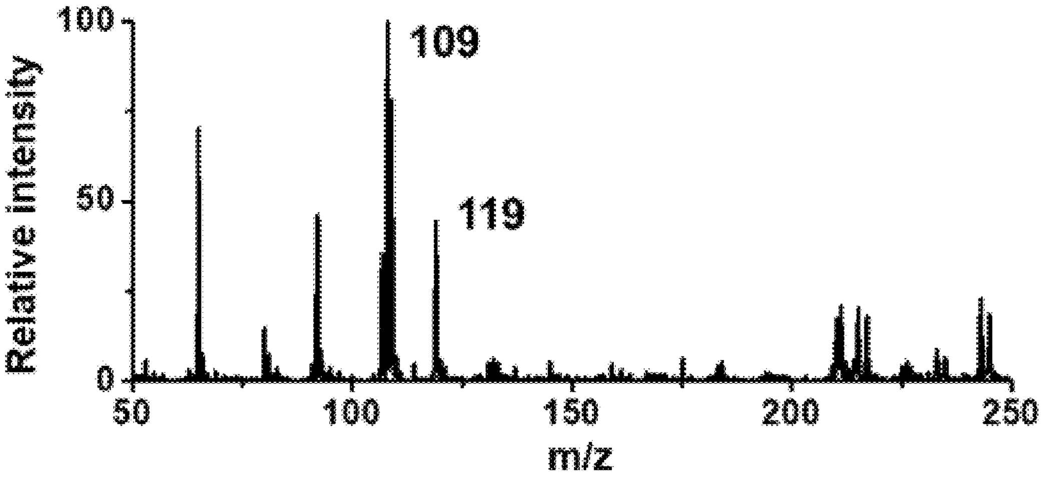
FIG. 22 shows mass spectrum of PDA/FA mixture in presence of HCl. Concentrations of reactants and of HCl were 8 mM. Similar CRs are observed with and without HCl.

We assessed the effect of decreasing the pH of the reaction mixture by adding equimolar concentrations of a strong inorganic acid, HCl. In the bulk PDA/FA reaction this addition does not help to improve significantly product formation. Similarly, in the case of the microdroplet reaction, addition of an equimolar concentration of HCl does not cause significant changes in the mass spectrum of the reaction mixture (FIG. 22). This lack of observable effect of the pH reduction is consistent with the suggestion that the super acid at the surface of positively-charged water containing droplets is responsible for protonating the carboxylic acid. The addition of HCl will reduce the pH in the core of the droplet, but without changing the protonation of carboxylic acid.

Acceleration Factors

Figure 23:
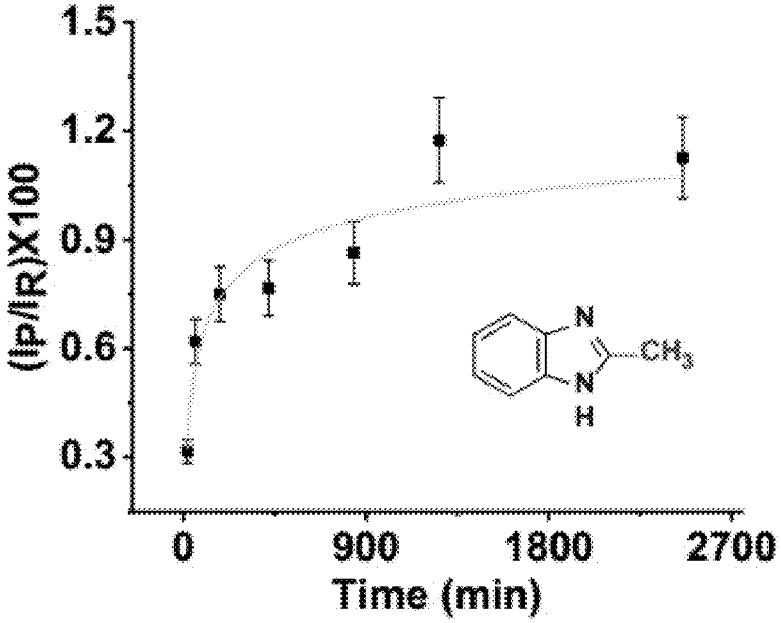
FIG. 23 shows product to reagent ion intensity ratio for the bulk reaction under ambient conditions for 2-methylbenzimidazole synthesis. Inset shows the molecular structure of the product. The starting concentrations of each reagent in the mixture was 8 mM. The reaction was performed in a closed 500 mL round bottom flask.

The apparent acceleration factor (AAF) of a reaction can be calculated by comparing the product to starting material intensity ratio in the microdroplet reaction to the value in the bulk reaction carried out for the same period of time, viz. ([P]\[SM])bulk\([P]\[SM]) droplet, or alternatively by recording the ratio of the times required to reach the same conversion ratio for both the conditions. To get a value for the AAF we performed a bulk reaction using an equimolar ratio of PDA and AA in methanol at ambient temperature. The AAF was calculated from the kinetic data plotted in FIG. 23. This simple method of approximating the apparent acceleration factor (not the true acceleration factor which is the ratio of rate constants) shows that the microdroplet reaction is accelerated by a very large factor (almost 109). This is not intended as a qualitative measure as because the role of the inlet temperature in driving the reaction has not been considered.

Figure 24:
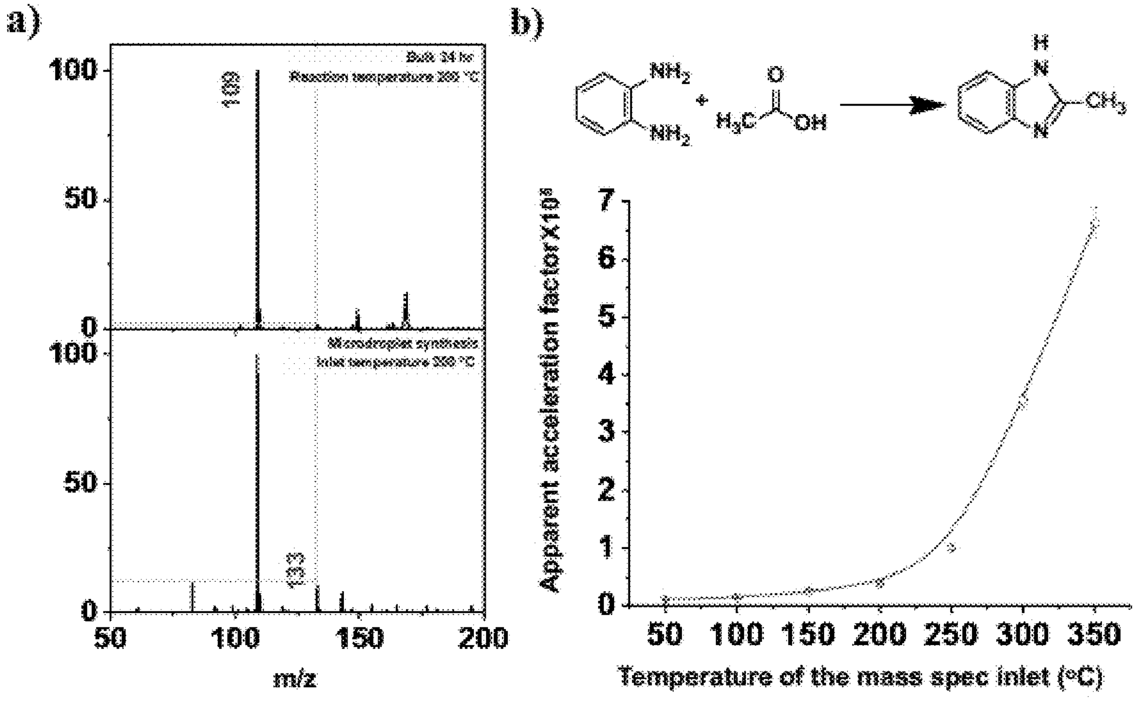
FIG. 24 panels A-B show effect of inlet temperature on accelerated formation of 2-methylbenzimidzaole (m/z 133) from phenylenediamine (m/z 109). Panel A) Comparative mass spectra of bulk reaction mixture at 200° C. for 24 h and microdroplet synthesis at 200° C. inlet temperature. Panel B) Temperature vs reaction rate acceleration factor. Inset shows the reaction scheme.

It is expected that the AAF will increase with temperature, as we have seen that the relative intensity of product increases sharply above 270° C. inlet temperature. To account for this, we compared high temperature microdroplet data with bulk reaction data obtained by refluxing at 200° C. set temperature for 24 hours. Comparison of this 200° C. bulk with microdroplet reactions at 200° C. inlet temperature (FIG. 24 panel A) shows that the relative intensity of the product peak at m/z 133 is significantly lower in the bulk than in the microdroplet experiment. This difference becomes even more significant with higher inlet temperatures, which provide exponentially larger reaction acceleration factors (FIG. 24 panel B). The apparent acceleration factor at 50° C. inlet temperature was $1.8\times10^{9}$ and this increases to $5.5\times10^{9}$ at 350° C. This is just one example of a very high AAF, others are shown later in the article and factors of similar magnitude have been reported for the Biginolli reaction where there we similar temperature effects associated with the last step of a reaction.

Scope of Ambient Droplet Reaction

The results of a systematic study of the scope of the microdroplet synthesis of benzimidazoles at ambient temperature was performed using EESI. This procedure not only allows the entire reaction to occur at ambient temperature but it also allows ready scale up to several hundred mg. MS and NMR were used to characterize and quantify the reaction products which were collected on a surface rather than being directly transferred into the MS. The results are summarized in Table 1, which gives the experimental conversion ratio (CR), the apparent acceleration factor (AAF) and the experimentally determined yield, as measured after isolation.

TABLE 1

Scope of microdroplet synthesis of benzimidazoles from substituted o-aromatic diamines and aromatic/aliphatic carboxylic acids[a]

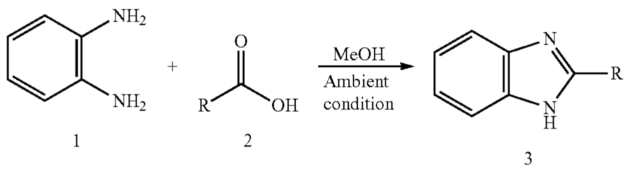

1 2 3

| Entry | Diamine (1) | Acid (2) | Product (3) | AAF ($x10^{0}$) | CR | Yield (%) |
|---|---|---|---|---|---|---|
| 1 | 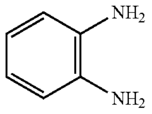 | 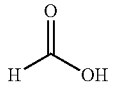 | 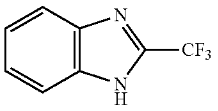 5a | 0.83 | 30 | 72 |
| 2 | 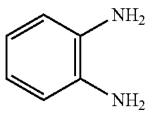 | 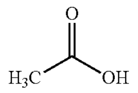 | 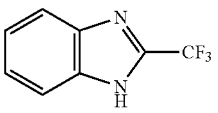 5b | 0.74 | 10 | 16 |

TABLE 1-continued
Scope of microdroplet synthesis of benzimidazoles from substituted o-aromatic diamines and aromatic/aliphatic carboxylic acids[a]
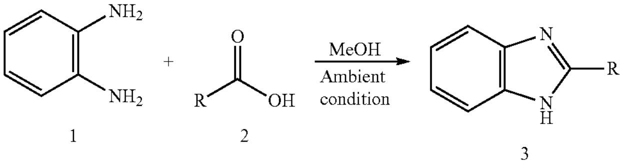
1 2 3
| Entry | Diamine (1) | Acid (2) | Product (3) | AAF $(x10^{0})$ | CR | Yield (%) |
|---|---|---|---|---|---|---|
| 3 | 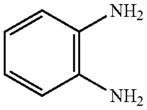 | 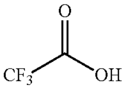 | 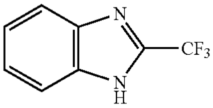 5c | 0.11 | 19 | 22 |
| 4 | 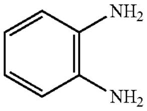 | 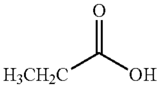 | 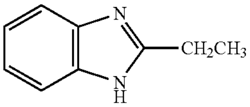 5d | 25 | 1 | 10 |
| 5 | 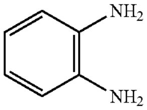 | 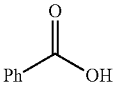 | 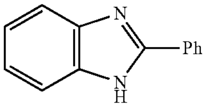 5e | 0.02 | 4 | 5 |
| 6 | 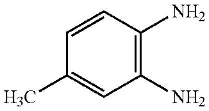 | 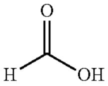 | 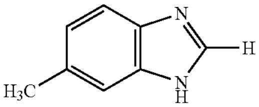 5f | 0.25 | 62 | 93 |
| 7 | 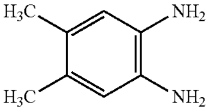 | 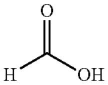 | 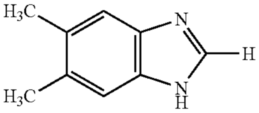 5g | 4.2 | 4 | 38 |
| 8 | 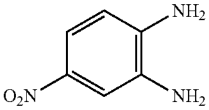 | 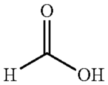 | 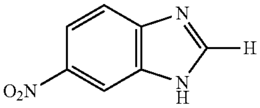 5h | No reaction | No reaction | No reaction |
| 9 | 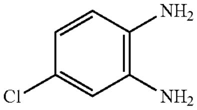 | 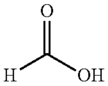 | 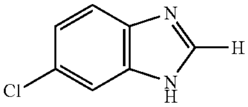 5i | 0.59 | 15 | 60 |
| 10 | 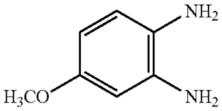 | 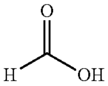 | 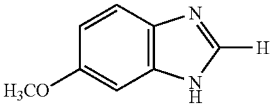 5j | 0.04 | 48 | 67 |

TABLE 1-continued

Scope of microdroplet synthesis of benzimidazoles from substituted o-aromatic diamines and aromatic/aliphatic carboxylic acids[a]

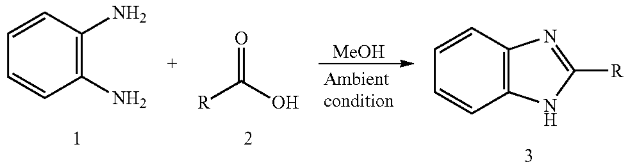

1 2 3

| Entry | Diamine (1) | Acid (2) | Product (3) | AAF ($x10^9$) | CR | Yield (%) |
|---|---|---|---|---|---|---|
| 11 | 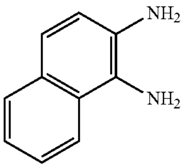 [SMILES: Nc1ccc2ccccc2c1N] | 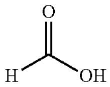 | 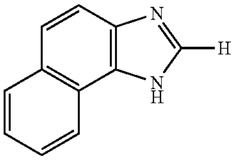 5k | 200 | 6 | 29 |

[a]The reactions were performed using a home built ESSI source.
Each diamine (200 mg) was used in a 1:1 molar ratio with the acid in methanol.
The flow rate and the gas pressure used for droplet deposition were 10 μL/min and 30 psi.
The ESSI experiment was done under ambient conditions (in contrast to the nESI data reported above, which used an inlet temperature of 50° C. unless otherwise indicated).
In a few cases the CR and the yield trends differ, likely due to poor product separation by flash chromatography.

Figure 25:
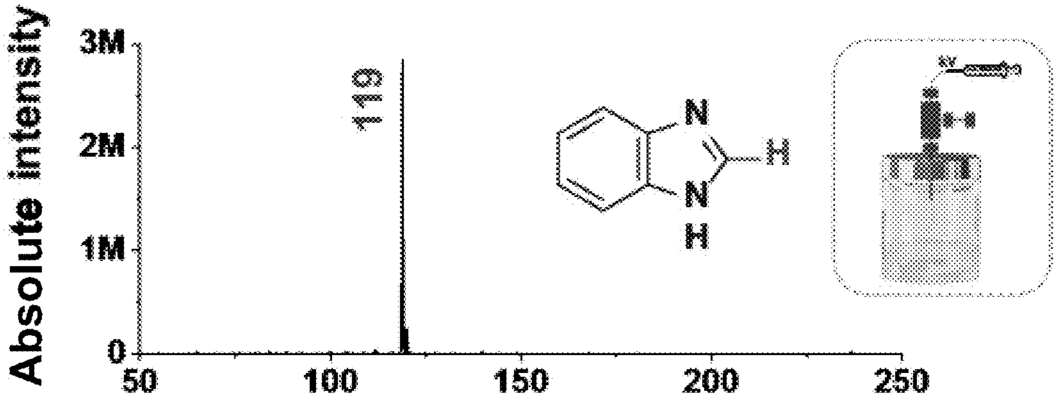
FIG. 25 shows mass spectrum of the isolated product after benzimidazole synthesis by spray deposition with diagram that depicts the spray deposition reaction setup. The crude mixture was separated using flash column chromatography. Yield was determined to be about 72%.
Figure 26:
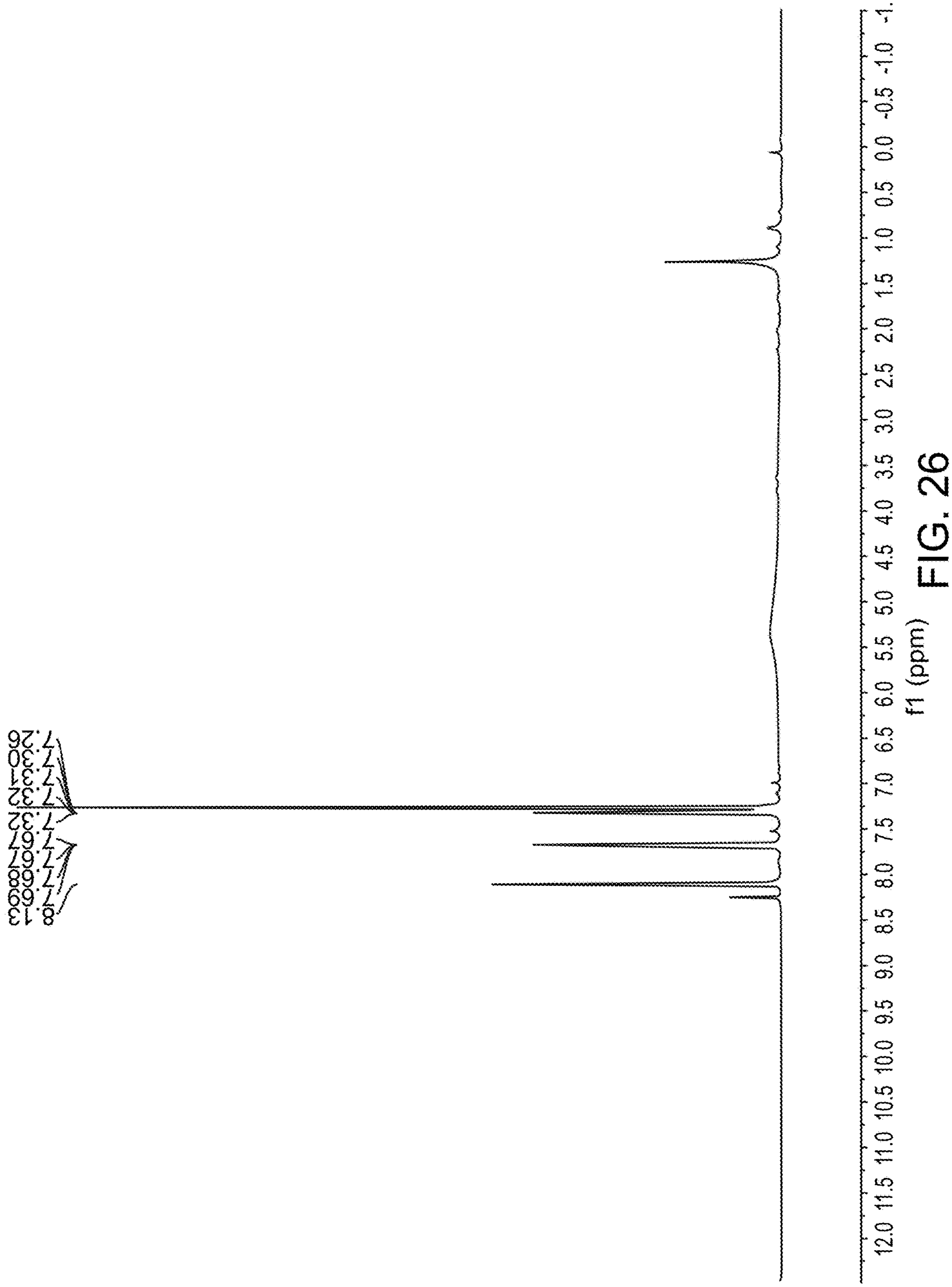
FIG. 26 shows NMR of the isolated product for the deposited sample for the benzimidazole synthesis. 1H NMR (400 MHz, CDCl3) δ 8.24 (s, 1H), 8.10 (s, 6H), 7.68 (dd, J=6.1, 3.2 Hz, 11H), 7.31 (dd, J=6.1, 3.2 Hz, 11H), 7.26 (s, 18H), 1.25 (s, 5H). Peak at 7.26 ppm is the solvent peak.
Figure 27:
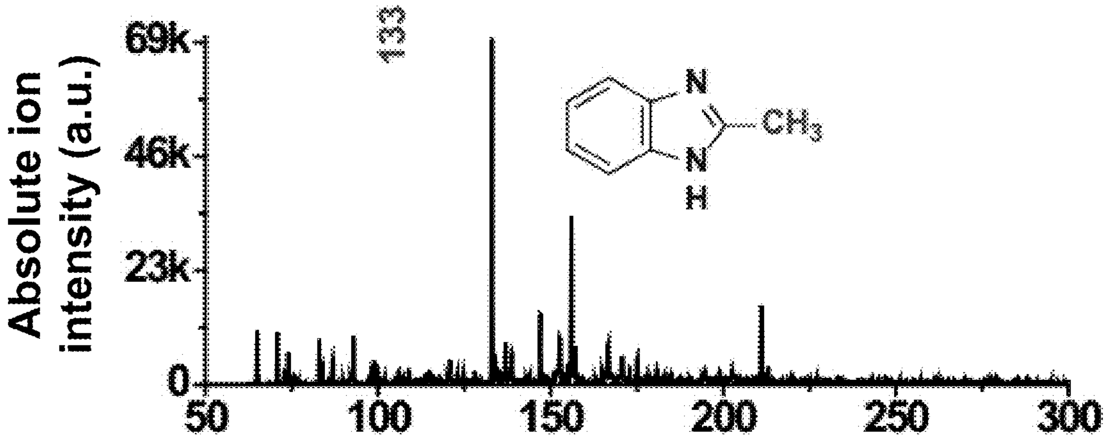
FIG. 27 shows mass spectrum of the isolated product of the deposited sample for the 2-benzimidazole synthesis. Low isolated yield resulted in noise in the mass spectrum.
Figure 28:
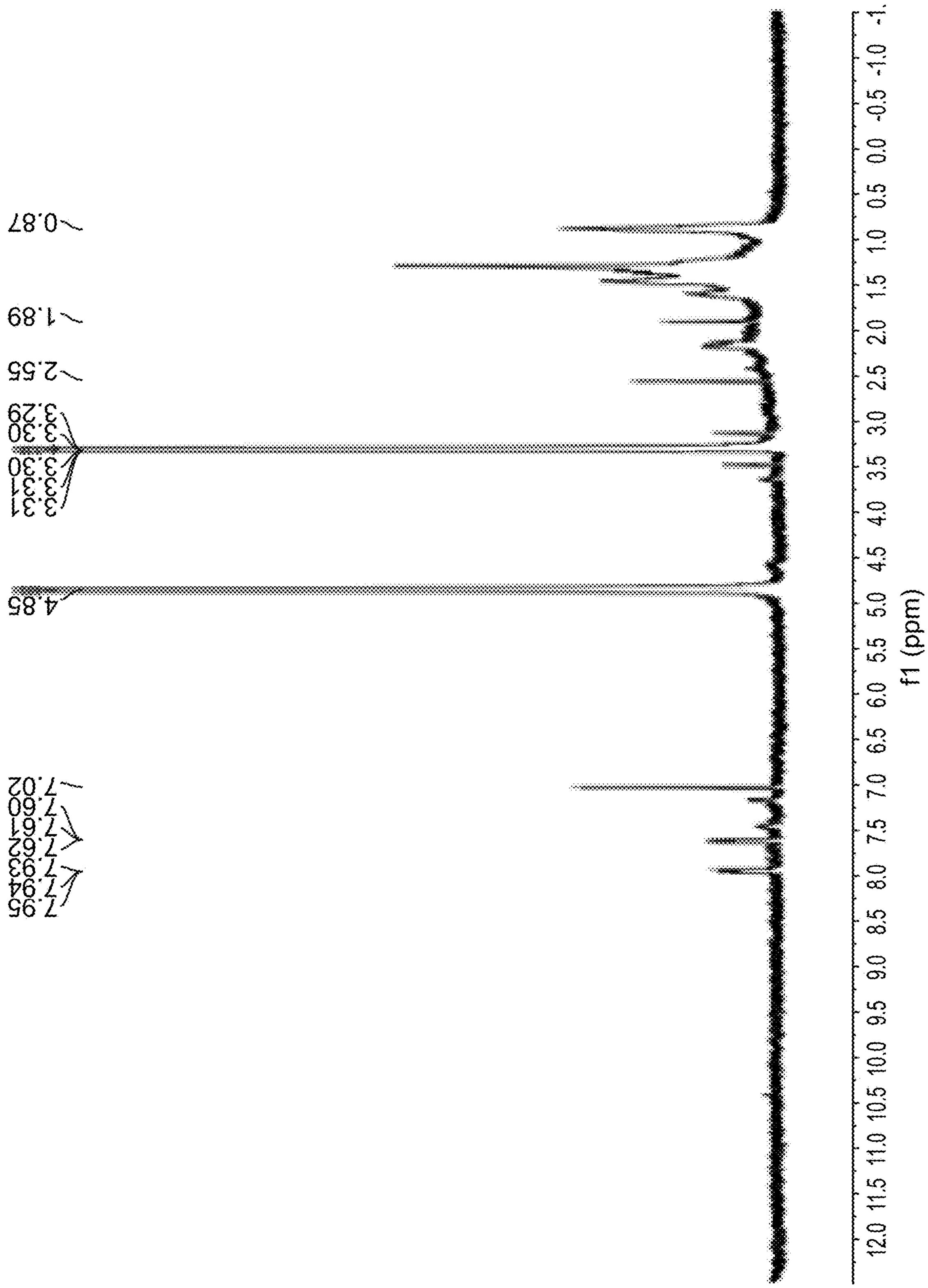
FIG. 28 shows 1H NMR for the isolated product of the deposited sample for the 2-methylbenzimidazole synthesis. 1H NMR (400 MHz, MeOD) δ 7.96-7.91 (m, 2H), 7.65-7.58 (m, 1H), 7.02 (s, 2H), 2.55 (s, 1H). Peaks at 4.85 and 3.29-3.31 ppm are solvent peaks while other minor peaks are from impurities.

The mass spectra typically show a single peak due to the product with no trace of reagents or intermediates, as typified by benzimidazole (FIG. 25). The 1H NMR of this isolated product is presented in FIG. 26. We found the actual yield of the product of benzimidazole synthesis to be 72% (5a, Table 1). However, the yield was reduced to 16% in the case of 2-methylbenzimidazole (5b, Table 1). This is due to the inductive effect of the methyl group in the carboxylic acid, which weakens the electrophilic center of the acid. MS and NMR spectra are presented in FIGS. 27-28. Product isolation was carried out using flash chromatography, which was not effective in separating all the products as reflected in the mass as well as in the NMR spectra. Other 2-substituted benzimidazoles were synthetized by varying the carboxylic acids. An electron withdrawing group such as $CF_3$— in the carboxylic acid increases the yield to 22% (5c, Table 1). The ethyl substituted benzimidazole (5d, Table 1) has a 10% yield, similar to the methyl substituted case. Correspondingly, the phenyl substituent on the carboxylic acid provides a lower yield (5%) due to resonance electron donation.

The reaction scope was further extended by performing reactions between FA and several substituted o-aryl diamines, specifically: 4-methyl-1,2-phenyldiamine, 4,5-dimethyl-1,2-phenyldiamine, 4-nitro-1,2-phenyldiamine, 4-chloro-1,2-phenyldiamine, 4-methoxy-1,2-phenyldiamine and 1,2-diaminonapthalene, to synthesize 4-methylbenzimidazole (5f), 4,5-dimethylbenzimidazole (5g), 4-nitrobenzimidazole (5h), 4-chlorobenzimidazole (5i), 4-methoxybenzimidazole (5j), and naphth[1,2]imidazole (5k), respectively (entries 4-9 in Table 1). It is observed that for the first two cases the inductive effect facilitates product formation leading to a 93 and 36% product yield. We suspect that a steric effect reduces the product yield in case of the dimethyl substituted amine. However, a conjugated strong electron withdrawing group (nitro-) results in no product formation (5h, Table 1), while the chloro- and the methoxy-substituted products (5i and 5j, Table 1) have yields of 62% and 67%, respectively. We also extended the method to the synthesis naphth[1,2]imidazole (51, Table 1) and observed 29% of yield with very high AAF of the order of $2x10^{11}$.

There is a rough correlation between the experimentally observed isolated yields and the experimentally estimated acceleration factors (as seen in Table 1). There is also a rough agreement with electron donating/withdrawing character of the diamine and the carboxylic acid (with some exceptions potentially due to steric effects). The AAF for the benzimidazole synthesis ($0.83x10^9$) is in the same order of other reactions with substituted amines and carboxylic acids. However, the increase of AAF in case of the reactions of PDA/PA ($2.5x10^{10}$), 4,5-dimethylPDA/FA ($4.2x10^9$) and napthalene-1,2-diamine/FA ($2x10^{11}$) may be due to their low reactivity in bulk due to steric effects. The high yield (and conversion ratio) for the methoxydiaminobenzene (entry 10) is consistent with the expected high reactivity of the amine due the electron donation by the oxygen of the methoxyl group. These relationships provide strong evidence for the nucleophilic attack at the carboxylic acid carbon which must be ascribed to the extraordinary acidity at the droplet (and thin film) interfaces.

It is commonplace knowledge that amines and carboxylic acids react in Brønsted fashion to produce a salt, while amines react with carboxylic acid halides by nucleophilic substitution to give amides. The corresponding nucleophilic substitution with an acid would require the carboxylic acid to be protonated to give the conjugate base which could then eliminate water. This situation would call for extraordinary conditions in which a very strong acid is present so that not only is the ionization of the acid to its conjugated base suppressed by the common ion effect, but the neutral acid itself be protonated to react as a carbon-centered Lewis acid. These conditions are satisfied in the benzimidazole chemistry examined in this study.

Accelerated microdroplet synthesis of benzimidazole and its derivatives have been demonstrated under ambient conditions. The reaction involves aromatic-1,2-diamines and carboxylic acids in a metal free environment with no requirement of base to complete the product formation. Online mass spectrometric monitoring enables us to detect reaction intermediates and understand the reaction mechanism. Ten examples are shown to extend the scope of the microdroplet synthesis.

Spray Sources

In general, the systems of the invention can include a spray system in which pneumatics and optionally electrical potential are used to create a fine spray, for example an electrosonic spray ionization source, such as described for example in Takats et al. (Anal. Chem., 2004, 76 (14), pp 4050-4058), the content of which is incorporated by reference herein in its entirety. The skilled artisan will recognize that any source that generates a liquid spray discharge including small droplets (e.g., microdroplets), charged or uncharged, can be used with systems and methods of the invention.

Additional exemplary ionization sources include techniques that utilize ionization sources at atmospheric pressure for mass spectrometry include electrospray ionization (ESI; Fenn et al., Science, 246:64-71, 1989; and Yamashita et al., J. Phys. Chem., 88:4451-4459, 1984); atmospheric pressure ionization (APCI; Carroll et al., Anal. Chem. 47:2369-2373, 1975); and atmospheric pressure matrix assisted laser desorption ionization (AP-MALDI; Laiko et al. Anal. Chem., 72:652-657, 2000; and Tanaka et al. Rapid Commun. Mass Spectrom., 2:151-153, 1988). The content of each of these references in incorporated by reference herein its entirety.

Other exemplary mass spectrometry techniques that work with systems and methods of the invention utilize direct ambient ionization/sampling methods that include direct analysis in real time (DART; Cody et al., Anal. Chem., 77:2297-2302, 2005); Atmospheric Pressure Dielectric Barrier Discharge Ionization (DBDI; Kogelschatz, Plasma Chemistry and Plasma Processing, 23:1-46, 2003, and PCT international publication number WO 2009/102766), and electrospray-assisted laser desorption/ionization (ELDI; Shiea et al., J. Rapid Communications in Mass Spectrometry, 19:3701-3704, 2005). The content of each of these references in incorporated by reference herein its entirety.

In certain embodiments, microdroplets of a sample are generated using nanospray ESI. Exemplary nano spray tips and methods of preparing such tips are described for example in Wilm et al. (Anal. Chem. 2004, 76, 1165-1174), the content of which is incorporated by reference herein in its entirety. NanoESI is described for example in Karas et al. (Fresenius J Anal Chem. 2000 March-April; 366(6-7):669-76), the content of which is incorporated by reference herein in its entirety.

In certain embodiments, the probe is configured for inductive charging. Inductive electrospray ionization (iESI) is a variant of electrospray ionization (ESI) which accurately controls the creation of charged droplets by placing an electrode near a spray emitter and pulsing it repetitively to high positive potential. Inductive ESI provides several new capabilities: it is characterized by a remarkable tolerance to matrix and to salt effects and it has a high efficiency. iESI avoids the clogging problem because the DC voltage pulse circuit 'rings' by polarizing the solution first in one direction then in the opposite and avoiding product build up from electrochemical reactions and/or solvent evaporation at the spray tip. Inductive electrospray ionization is described for example in U.S. Pat. No. 9,184,036 and U.S. patent application publication number 2014/0051180, the content of each of which is incorporated by reference herein in its entirety.

Collection of Ions and/or Reaction Products without or after Mass-Selective Analysis Systems and methods for collecting ions or reaction products that have been analyzed by a mass spectrometer are shown in U.S. Pat. No. 7,361,311 and PCT/US2018/023747, the content of each of which is incorporated by reference herein in its entirety. In certain embodiments, ions and/or reaction products may be collected after mass analysis as described in Cooks (U.S. Pat. No. 7,361,311). In other embodiments, ions and/or reaction products may be collected in the ambient environment, at atmospheric pressure or under vacuum, without mass analysis. The collected ions and/or reaction products may then be subsequently analyzed by any suitable technique, such as infrared spectrometry or mass spectrometry.

Generally, the preparation of a microchip or substrate with an array of molecules, e.g., reaction products, first involves the production of a reaction product in the liquid droplet spray discharge, as described above. The ions and/or reaction products can then be focused and collected using methods described below or can first be separated based on their mass/charge ratio or their mobility or both their mass/charge ratio and mobility. For example, the ions and/or reaction products can be accumulated in an ion storage device such as a quadrupole ion trap (Paul trap, including the variants known as the cylindrical ion trap and the linear ion trap) or an ion cyclotron resonance (ICR) trap. Either within this device or using a separate mass analyzer (such as a quadrupole mass filter or magnetic sector or time of flight), the stored ions are separated based on mass/charge ratios. Additional separation might be based on mobility using ion drift devices or the two processes can be integrated. The separated ions and/or reaction products are then deposited on a microchip or substrate at individual spots or locations in accordance with their mass/charge ratio or their mobility to form a microarray.

To achieve this, the microchip or substrate is moved or scanned in the x-y directions and stopped at each spot location for a predetermined time to permit the deposit of a sufficient number of molecules of the and/or reaction product to form a spot having a predetermined density. Alternatively, the gas phase ions and/or reaction products can be directed electronically or magnetically to different spots on the surface of a stationary chip or substrate. The reaction products are preferably deposited on the surface with preservation of their structure, that is, they are soft-landed. Two facts make it likely that dissociation or denaturation on landing can be avoided. Suitable surfaces for soft-landing are chemically inert surfaces that can efficiently remove vibrational energy during landing, but which will allow spectroscopic identification. Surfaces which promote neutralization, rehydration or having other special characteristics might also be used for protein soft-landing.

Generally, the surface for ion and/or reaction product landing is located after the ion focusing device, and in embodiments where ions are first separated, the surface is located behind the detector assembly of the mass spectrometer. In the ion detection mode, the high voltages on the conversion dynode and the multiplier are turned on and the ions are detected to allow the overall spectral qualities, signal-to-noise ratio and mass resolution over the full mass range to be examined. In the ion-landing and/or reaction product-landing mode, the voltages on the conversion dynode and the multiplier are turned off and the ions and/or reaction products are allowed to pass through the hole in the detection assembly to reach the landing surface of the plate (such as a gold plate). The surface is grounded and the potential difference between the source and the surface is 0 volts.

An exemplary substrate for soft landing is a gold substrate (20 mm×50 mm, International Wafer Service). This substrate may consist of a Si wafer with 5 nm chromium adhesion layer and 200 nm of polycrystalline vapor deposited gold. Before it is used for ion landing, the substrate is cleaned with a mixture of $H_2SO_4$ and $H_2O_2$ in a ratio of 2:1, washed thoroughly with deionized water and absolute ethanol, and then dried at 150° C. A Teflon mask, 24 mmx 71 mm with a hole of 8 mm diameter in the center, is used to cover the gold surface so that only a circular area with a diameter of 8 mm on the gold surface is exposed to the ion beam for ion soft-landing of each mass-selected ion beam. The Teflon mask is also cleaned with 1:1 MeOH:$H_2O$ (v/v) and dried at elevated temperature before use. The surface and the mask are fixed on a holder and the exposed surface area is aligned with the center of the ion optical axis.

Any period of time may be used for landing of the ions and/or reaction products. In certain embodiments, between each ion-landing and/or reaction product-landing, the instrument is vented, the Teflon mask is moved to expose a fresh surface area, and the surface holder is relocated to align the target area with the ion optical axis. After soft-landing, the Teflon mask is removed from the surface.

In another embodiment a linear ion trap can be used as a component of a soft-landing instrument. Ions travel through a heated capillary into a second chamber via ion guides in chambers of increasing vacuum. The ions and/or reaction products are captured in the linear ion trap by applying suitable voltages to the electrodes and RF and DC voltages to the segments of the ion trap rods. The stored ions can be radially ejected for detection. Alternatively, the ion trap can be operated to eject the ions and/or reaction products of selected mass through the ion guide, through a plate onto the microarray plate. The plate can be inserted through a mechanical gate valve system without venting the entire instrument.

The advantages of the linear quadrupole ion trap over a standard Paul ion trap include increased ion storage capacity and the ability to eject ions both axially and radially. Linear ion traps give unit resolution to at least 2000 Thomspon (Th) and have capabilities to isolate ions of a single mass/charge ratio and then perform subsequent excitation and dissociation in order to record a product ion MS/MS spectrum. Mass analysis will be performed using resonant waveform methods. The mass range of the linear trap (2000 Th or 4000 Th but adjustable to 20,000 Th) will allow mass analysis and soft-landing of most molecules of interest. In the soft-landing instrument described above the ions are introduced axially into the mass filter rods or ion trap rods. The ions can also be radially introduced into the linear ion trap.

Methods of operating the above described soft-landing instruments and other types of mass analyzers to soft-land ions of different masses at different spots on a microarray are now described. The reaction products are introduced into the mass filter. Ions and/or reaction products of selected mass-to-charge ratio will be mass-filtered and soft-landed on the substrate for a period of time. The mass-filter settings then will be scanned or stepped and corresponding movements in the position of the substrate will allow deposition of the ions and/or reaction products at defined positions on the substrate.

The ions and/or reaction products can be separated in time so that the ions and/or reaction products arrive and land on the surface at different times. While this is being done the substrate is being moved to allow the separated ions and/or reaction products to be deposited at different positions. A spinning disk is applicable, especially when the spinning period matches the duty cycle of the device. The applicable devices include the time-of-flight and the linear ion mobility drift tube. The ions and/or reaction products can also be directed to different spots on a fixed surface by a scanning electric or magnetic fields.

In another embodiment, the ions and/or reaction products can be accumulated and separated using a single device that acts both as an ion storage device and mass analyzer. Applicable devices are ion traps (Paul, cylindrical ion trap, linear trap, or ICR). The ions and/or reaction products are accumulated followed by selective ejection of the ions for soft-landing. The ions and/or reaction products can be accumulated, isolated as ions of selected mass-to-charge ratio, and then soft-landed onto the substrate. Ions and/or reaction products can be accumulated and landed simultaneously. In another example, ions and/or reaction products of various mass-to-charge ratios are continuously accumulated in the ion trap while at the same time ions of a selected mass-to-charge ratio can be ejected using SWIFT and soft-landed on the substrate.

In a further embodiment of the soft-landing instrument, ion mobility is used as an additional (or alternative) separation parameter. As before, ions and/or reaction products are generated by a suitable ionization source, such as those described herein. The ions and/or reaction products are then subjected to pneumatic separation using a transverse air-flow and electric field. The ions and/or reaction products move through a gas in a direction established by the combined forces of the gas flow and the force applied by the electric field. Ions and/or reaction products are separated in time and space. The ions and/or reaction products with the higher mobility arrive at the surface earlier and those with the lower mobility arrive at the surface later at spaces or locations on the surface.

The instrument can include a combination of the described devices for the separation and soft-landing of ions and/or reaction products of different masses at different locations. Two such combinations include ion storage (ion traps) plus separation in time (TOF or ion mobility drift tube) and ion storage (ion traps) plus separation in space (sectors or ion mobility separator).

It is desirable that the structure of the reaction product be maintained during the soft-landing process. One such strategy for maintaining the structure of the reaction product upon deposition involves keeping the deposition energy low to avoid dissociation or transformation of the ions and/or reaction products when they land. This needs to be done while at the same time minimizing the spot size. Another strategy is to mass select and soft-land an incompletely desolvated form of the ionized molecules and/or reaction products. Extensive hydration is not necessary for molecules to keep their solution-phase properties in gas-phase. Hydrated molecular ions and/or reaction products can be formed by electrospray and separated while still "wet" for soft-landing. The substrate surface can be a "wet" surface for soft-landing, this would include a surface with as little as one monolayer of water. Another strategy is to hydrate the molecule and/or reaction product immediately after mass-separation and prior to soft-landing. Several types of mass spectrometers, including the linear ion trap, allow ion/molecule reactions including hydration reactions. It might be possible to control the number of water molecules of hydration. Still further strategies are to deprotonate the mass-selected ions using ion/molecule or ion/ion reactions after separation but before soft-landing, to avoid undesired ion/surface reactions or protonate at a sacrificial derivatizing group which is subsequently lost.

Different surfaces are likely to be more or less well suited to successful soft-landing. For example, chemically inert surfaces which can efficiently remove vibrational energy during landing may be suitable. The properties of the surfaces will also determine what types of in situ spectroscopic identification are possible. The ions can be soft-landed directly onto substrates suitable for MALDI. Similarly, soft-landing onto SERS-active surfaces should be possible. In situ MALDI and secondary ion mass spectrometry can be performed by using a bi-directional mass analyzer such as a linear trap as the mass analyzer in the ion deposition step and also in the deposited material analysis step.

Mass Spectrometry Interface

In certain embodiments, the systems of the invention may be interfaced with a mass spectrometer, such as a bench-top or miniature mass spectrometer, such as described for example in Gao et al. (Z. Anal. 15 Chem. 2006, 78, 5994-6002), Gao et al. (Anal. Chem., 80:7198-7205, 2008), Hou et al. (Anal. Chem., 83:1857-1861, 2011), Sokol et al. (Int. J. Mass Spectrom., 2011, 306, 187-195), Xu et al. (JALA, 2010, 15, 433-439); Ouyang et al. (Anal. Chem., 2009, 81, 2421-2425); Ouyang et al. (Ann. Rev. Anal. Chem., 2009, 2, 187-25 214); Sanders et al. (Euro. J. Mass Spectrom., 2009, 16, 11-20); Gao et al. (Anal. Chem., 2006, 78(17), 5994-6002); Mulligan et al. (Chem.Com., 2006, 1709-1711); and Fico et al. (Anal. Chem., 2007, 79, 8076-8082), the content of each of which is incorporated herein by reference in its entirety.

An exemplary miniature mass spectrometer is described, for example in Gao et al. (Anal. Chem. 2008, 80, 7198-7205.), the content of which is incorporated by reference herein in its entirety. In comparison with the pumping system used for lab-scale instruments with thousands of watts of power, miniature mass spectrometers generally have smaller pumping systems, such as a 18 W pumping system with only a 5 L/min (0.3 m3/hr) diaphragm pump and a 11 L/s turbo pump for the system described in Gao et al. Other exemplary miniature mass spectrometers are described for example in Gao et al. (Anal. Chem., 2008, 80, 7198-7205.), Hou et al. (Anal. Chem., 2011, 83, 1857-1861.), PCT/US17/26269 to Purdue Research Foundation, and Sokol et al. (Int. J. Mass Spectrom., 2011, 306, 187-195), the content of each of which is incorporated herein by reference in its entirety.

The mass spectrometer may be interfaced online with the system or used off-line. In online embodiments, a tube can be connected to the reaction chamber and/or the condenser and/or the recirculation line. A portion of the solvent is diverted from the system and to the mass spectrometer. In such embodiment, the flow can go directly into another pneumatic sprayer, including a paper spray probe as described for example in U.S. Pat. No. 8,859,956, the content of which is incorporated by reference herein in its entirety, in order to generate a discharge that can be sent into the mass spectrometer.

In off-line embodiments, a portion of solvent is obtained from the electrostatic precipitator, the condenser, or the recirculation line and then analyzed by mass spectrometry.

EXAMPLES

Example 1: Online Reaction Monitoring

Online monitoring (as described for example in U.S. Pat. No. 9,500,623, the content of which is incorporated by reference herein in its entirety) was carried out using a nESI source in which the reagents were mixed prior to being sprayed. The nESI tip (5 μm diameter) was held 1 cm away from the inlet of the mass spectrometer. The applied potential for spray generation was kept at 2-2.5 kV. The capillary and tube lens voltages were set to 50 and 100 V, respectively. For the temperature dependence study, the capillary temperature was initially set to 50° C. but later increased to a final temperature of 400° C. Unless otherwise noted, the mass spectrometric studies were performed at 50° C. inlet temperature. All mass spectra were recorded by averaging 4 microscans at 100 ms scan times. A linear ion trap was used for all MS studies, and CID with He as collision gas was used for MS/MS analysis.

Example 2: Thin Film Synthesis

Thin film reactions were performed by applying a thin film of the reactants onto the surface of parafilm. The parafilm was wrapped around a glass slide to prevent extraneous catalysis by the glass. The thin film of reaction mixture was produced by drop-casting 5 μL of mixture containing 2.5 ppm of p-toluenesulfonic acid onto the parafilm surface. The film was allowed to dry slowly in ambient air. Sampling was done by transferring the crude product into 10 μL of methanol and then quenching by diluting the sample ×10 in methanol before measuring by nESI. Measurements at different times were done using different thin films. All thin film reactions were performed in triplicate to verify reproducibility.

Example 3: Scaled-Up Reactions and Product Isolation

Scaling-up and product deposition was done using ambient ESSI. Scale-up was achieved by increasing the flux of droplets by increasing the flow rate of the solution in a fused silica capillary (150 μm of ID and 300 μm of OD). A flow rate of 10 μL/min was used with +3 kV applied potential and 30 psi nebulization N2 gas pressure. The amount of starting material used for the deposition experiment was 200 mg in each case. The collected crude product mixture was dissolved in methanol to perform thin layer chromatography to allow optimization of the solvent system for better separation of product from the crude. With this information the crude reaction mixture was separated using normal-phase silica flash column chromatography in a Biotage automated flash chromatography column. A methanol and DCM solvent gradient was selected for the column chromatography based on the Rf value of the reagent and the product. The fractionated solutions were characterized using nESI MS and 1H NMR. The fractions which contained the product were mixed and solvent was removed at reduced pressure to obtain isolated solid product. Yields of the microdroplet reactions were calculated using the mass of the recovered solid.

Example 4: Bulk Synthesis

The bulk synthesis of 2-methylbenzimidazole was performed by mixing equimolar methanolic solutions of PDA and AA in a 500 mL two-neck round bottom flask with a condenser. The final concentrations of each reagent in the mixture was 8 mM. The reaction mixture was then stirred at 200° C. in a sand bath with continuous heating. The time dependent studies were carried out by removing 15 μL aliquots of sample at fixed time intervals. The reaction was heated and stirred for 24 hours. Bulk reactions were also carried out under ambient conditions and characterized in a similar way.

Monitoring of time dependent mass spectra of the bulk reaction mixture was performed after dilution. The dilution was done to quench the reaction as well as to avoid microdroplet synthesis. Inlet temperature was also set to 50° C. and the tip of the nESI emitter was kept as close as possible to the inlet of the mass spectrometer to prevent reaction during analysis. The applied potential to generate the electrospray plume was 1 kV. ([P][SM])bulk data of the 24-hour sample was used to calculate the acceleration factor.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A method of coupling a protonated carbon containing moiety to an ortho amine containing moiety to form a benzimidazole reaction product, the method comprising: generating a microdroplet comprising a protonated carbon containing moiety and an ortho amine containing moiety, wherein the microdroplet comprises an acidic surface that facilitates a reaction between the protonated carbon containing moiety and the ortho amine containing moiety and generates a benzimidazole reaction product comprising a carbon-nitrogen bond via the amine of the amine containing moiety, wherein the carbon containing moiety comprises a protonated carboxylic acid, with the proviso that the ortho amine containing moiety does not contain a strong electron withdrawing group.

2. The method of claim 1, wherein generating the microdroplet is by use of an electrospray probe or nano-electrospray probe.

3. The method of claim 1, wherein the microdroplet generates an environment that accelerates a rate of the reaction as compared to the same reaction occurring outside of a microdroplet environment.

4. The method of claim 1, wherein the method further comprises analyzing the reaction product in a mass spectrometer by directing the microdroplets into the mass spectrometer.

5. The method of claim 1, wherein the method further comprises collecting the reaction product by directing the microdroplets onto a surface.

6. The method of claim 1, wherein the method is conducted without use of a metal or metal catalyst.

7. The method of claim 6, wherein the method is conducted without use of a base.

8. The method of claim 6, wherein the amine containing moiety comprises an aromatic-1,2-diamine.

9. A method of producing a benzimidazole, the method comprising: generating a microdroplet comprising a carboxylic acid and an aromatic-1,2-diamine, wherein the microdroplet comprises an acidic surface that facilitates a reaction between the carboxylic acid and the aromatic-1,2-diamine and generates a benzimidazole.

10. The method of claim 9, wherein generating the microdroplets is by use of an electrospray probe or nanoelectrospray probe.

11. The method of claim 9, wherein microdroplet generates an environment that accelerates a rate of the reaction as compared to the same reaction occurring outside of a microdroplet environment.

12. The method of claim 1, wherein the method further comprises analyzing the benzimidazole in a mass spectrometer by directing the microdroplets into the mass spectrometer.

13. The method of claim 9, wherein the method further comprises collecting the benzimidazole by directing the microdroplets onto a surface.

14. The method of claim 1, wherein the method is conducted without use of a metal or metal catalyst.

15. The method of claim 14, wherein the method is conducted without use of a base.

16. The method of claim 9, wherein there is a 1:1 molar ratio of the aromatic-1,2-diamine and the carboxylic acid.

17. The method of claim 9, wherein a solvent in the microdroplet is methanol.

18. The method of claim 9, wherein:

the aromatic-1,2-diamine is at least one selected from the group consisting of: 1,2-phenyldiamine (PDA), 4-methyl-1,2-phenyldiamine, 4,5-dimethyl-1,2-phenyldiamine, 4-nitro-1,2-phenyldiamine, 4-chloro-1,2-phenyldiamine, 4-methoxy-1.2-phenyldiamine, 1,2-diaminonapthalene); and the carboxylic acid is at least one selected from the group consisting of: (formic acid (FA), acetic acid (AA), trifluoroacetic acid (TFAA), propanoic acid (PA) and benzoic acid (BA)).

* * * * *